United States Patent [19]

Rubin

[11] Patent Number: 5,523,502
[45] Date of Patent: Jun. 4, 1996

[54] FLEXIBLE LIGHT OLEFINS PRODUCTION

[75] Inventor: Jacob N. Rubin, Newton Hglds., Mass.

[73] Assignee: Stone & Webster Engineering Corp., Boston, Mass.

[21] Appl. No.: 151,342

[22] Filed: Nov. 10, 1993

[51] Int. Cl.$^6$ ........................................ C07C 4/06
[52] U.S. Cl. ................. 585/324; 585/314; 585/315; 585/330; 585/648; 585/651; 568/697
[58] Field of Search .................. 585/648, 310, 585/314, 315, 324, 330, 651; 568/697

[56] References Cited

U.S. PATENT DOCUMENTS

| | | | |
|---|---|---|---|
| 3,431,316 | 3/1969 | Banks | 260/683 |
| 3,485,890 | 12/1969 | Dixon | 260/683 |
| 3,763,032 | 10/1973 | Banks | 208/93 |
| 4,211,885 | 7/1980 | Banks | 585/316 |
| 4,255,605 | 3/1981 | Dixon | 585/332 |
| 4,423,264 | 12/1983 | Juguin et al. | 585/255 |
| 4,542,249 | 9/1985 | Reusser | 585/329 |
| 4,559,320 | 12/1985 | Reusser | 502/251 |
| 4,575,575 | 3/1986 | Drake et al. | 585/646 |
| 4,620,053 | 10/1986 | Welch | 585/664 |
| 4,692,430 | 9/1987 | Welch | 502/342 |
| 4,749,819 | 6/1988 | Hamilton, Jr. | 585/329 |
| 4,780,436 | 10/1988 | Raatz et al. | 502/66 |
| 4,795,734 | 1/1989 | Chauvin et al. | 502/355 |
| 4,900,347 | 2/1990 | McCue, Jr. et al. | 62/24 |
| 4,980,053 | 12/1990 | Li et al. | 208/120 |
| 5,026,935 | 6/1991 | Leyshon et al. | 585/315 |
| 5,026,936 | 6/1991 | Leyshon et al. | 585/315 |
| 5,035,732 | 7/1991 | McCue, Jr. | 62/24 |
| 5,093,540 | 3/1992 | Forschner et al. | 585/324 |
| 5,159,127 | 10/1992 | Forschner et al. | 585/324 |
| 5,191,144 | 3/1993 | Le et al. | 585/643 |

OTHER PUBLICATIONS

Superflex Process, ARCO Chemical Technology Inc.
FCC/DCC Light Olefin Generator, 9th Ethylene Forum May 12–14, 1993 Woodlands, Texas.

*Primary Examiner*—P. Achutamurthy
*Attorney, Agent, or Firm*—Hedman, Gibson & Costigan

[57] ABSTRACT

A novel process having improved flexibility in olefins production is provided which integrates a deep catalytic cracking process with a steam cracking process, and optionally, also including steps of disproportionation and $C_4$ hydrocarbon processing including methyl tertiary butyl ether synthesis.

47 Claims, 9 Drawing Sheets

FLEXIBLE LIGHT OLEFINS PRODUCTION

The present invention relates to a method for producing olefins. More particularly, the present invention relates to an improved method for improving olefin product selectivity. Most particularly, the present invention relates to a method for producing olefins comprising steps of deep catalytic cracking, steam cracking, disproportionation and olefins purification.

BACKGROUND OF THE PRESENT INVENTION

Olefins have long been desired as feedstocks for the petrochemical industries. Olefins such as ethylene, propylene and the butylenes are useful in preparing a wide variety of petrochemicals, including, but not limited to, methyl tertiary butyl ether and polymers. Accordingly, a large number of processes, described in the literature, are directed to the production of olefins.

This is especially the case in recent years where there is an increasing demand for light olefinic gases with shrinking supplies of suitable feedstocks for producing such olefins. Thus, the petrochemical industry is continuously looking for processes which can provide for improved flexibility in producing various olefins from hydrocarbon feedstocks.

For example, Leyshon et al., U.S. Pat. No. 5,026,936 teaches a process for the preparation of propylene from $C_4$ or higher feeds by a combination of cracking and metathesis wherein the higher hydrocarbon is cracked to form ethylene and propylene and at least a portion of the ethylene is metathesized to propylene. See also, Leyshon et al., U.S. Pat. No. 5,026,935.

However, despite the prior art teachings there remains a need in the art to provide a more flexible method of selectively producing higher yields of olefins from various hydrocarbon feedstocks. None of the prior art teachings suggest the integration of a deep catalytic cracking process with a steam cracking process to improve flexibility in the olefin product slate. Unexpectedly, the integration of these processes results in significantly improved flexibility in producing desired olefins. Still further unexpected benefits are obtained by processing the cracked product effluents in downstream olefins purification, disproportionation and skeletal isomerization steps.

SUMMARY OF THE PRESENT INVENTION

It is therefore an object of the present invention to provide a process for the production of olefins.

It is another object of the present invention to provide a process for producing olefins from various hydrocarbon feedstocks.

It is still another object of the present invention to provide a flexible integrated process for selectively producing desired olefins.

It is a further object of the present invention to integrate a deep catalytic cracking process with a steam cracking process, or other non-catalytic cracking process, to provide flexibility in olefin production.

It is a still further object of the present invention to provide improved yields of ethylene and butylenes by employing a disproportionation process in combination with the integrated deep catalytic and steam cracking processes.

It is still another further object of the present invention to provide improved yields of propylene by employing a disproportionation process in combination with the integrated deep catalytic and steam cracking processes.

It is a still further object of the present invention to provide for improved yields of methyl tertiary butyl ether from the effluents from hydrocarbon feedstocks by combining the integrated deep catalytic and steam cracking processes with one or more synthesis and purification methods.

These and other objects are provided by the present invention.

DETAILED DESCRIPTION OF THE PRESENT INVENTION

Figure 1:
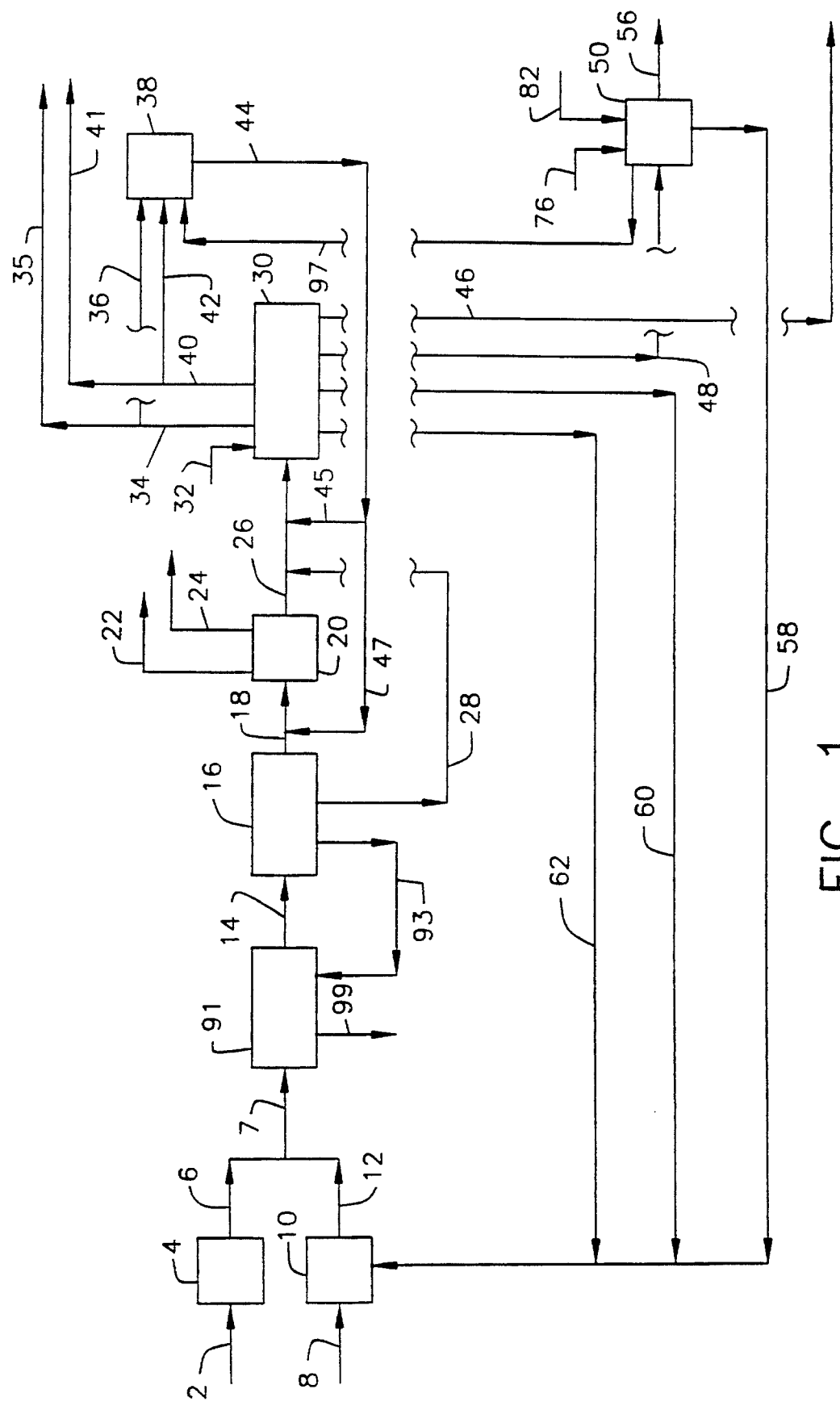
FIG. 1 depicts in flow chart form an embodiment of the present invention.

The present invention in its simplest form provides for the flexible production of olefins by integrating a deep catalytic cracking process with a non-catalytic cracking process, preferably steam cracking. These integrated cracking processes can then be combined with olefin purification processes, disproportionation processes and $C_4$ hydrocarbon processing such as one or more of methyl tertiary butyl ether synthesis, skeletal isomerization and hydroisomerization processes to selectively provide a wide variety of olefins and olefins products.

The deep catalytic cracking process is known in the art. In the deep catalytic cracking (DCC) process, described in Li et al., U.S. Pat. No. 4,980,053, a preheated hydrocarbon feedstock is cracked over a heated solid acidic catalyst in a reactor at temperatures ranging from about 500° C. to about 650° C., preferably from about 550° C. to about 620° C. The weight hourly space velocity of the charge may range from about 0.2 to about 20 $hr^{-1}$, preferably from about 1 to about 10 $hr^{-1}$. The catalyst-to-oil ratio may vary from about 2 to about 12, preferably from about 5 to about 10. In order to lower the partial pressure of hydrocarbon feed, steam or other gases, such as the dry gas of a catalytic cracking unit, may be added into the reactor during the conversion process.

When steam is used, a weight ratio of steam to hydrocarbon feed is preferably maintained at from about 0.01 to about 2:1. The total pressure of the reaction preferably ranges from about $1.5 \times 10^5$ to about $3 \times 10^5$ Pa, more preferably from about $1.5 \times 10^5$ to about $2 \times 10^5$ Pa.

After the reaction, the spent catalyst particles may be steam stripped to remove residual hydrocarbons absorbed on the catalyst as is known in the art. The spent catalyst particles with coke deposited thereon are then transferred to a regeneration zone as is also well known to those of ordinary skill in the art. Regeneration is generally conducted by contacting the catalyst with an oxygen-containing gas at a temperature of from about 650° C. to about 750° C. Afterwards the regenerated catalyst is typically recycled to the reaction zone.

Hydrocarbon feedstocks useful in the DCC process of the present invention may vary in a wide range, and typically are relatively heavy hydrocarbon feedstocks such as those selected from petroleum fractions with different boiling ranges, i.e., naphtha, distillate, vacuum gas oil, residual oil and mixtures thereof. Crude oil may also be directly used.

Catalysts used in the deep catalytic cracking process step of the present invention are solid, acidic catalysts comprising one or more active components and a matrix material. The active components include amorphous aluminosilicates or zeolites such as pentasil shape ultrastable hydrogen Y sieves, faujasite, rare earth cation exchanged faujasite, chemically treated and/or stabilized faujasite and mixtures thereof. The matrix material includes synthetic inorganic oxides and mineral clays. All of these catalysts are commercially available. See, U.S. Pat. No. 4,980,053.

Exemplary of the useful catalysts are pentasil shape molecular sieves, rare earth exchanged Y sieves (REY) containing catalysts, pentasil shape molecular sieves supported on kaolinite, amorphous aluminosilicates and mixtures of any of the foregoing.

The use of these catalysts at the specified reaction conditions provides for high yields of gaseous olefins, especially propylene and butylenes, by enhancing a secondary cracking reaction, reducing a hydrogen transfer reaction and prolonging the contact time between the hydrocarbon feed and the catalyst.

The steam cracking process and other non-catalytic cracking processes are well known to those of ordinary skill in the art. Steam cracking processes are generally carried out in radiant furnace reactors at elevated temperatures for short residence times while maintaining a low reactant partial pressure, relatively high mass velocity, and effecting a low pressure drop through the reaction zone. Any of the furnaces known to those skilled in the art may be employed, e.g., Palchik et al., U.S. Pat. No. 3,274,978; Hallee et al., U.S. Pat. No. 3,407,789; Woebcke, U.S. Pat. No. 3,820,955; Alagy et al., U.S. Pat. No. 4,780,196; DiNicolantonio, U.S. Pat. No. 4,499,055; Martens, U.S. Pat. No. 4,762,958 and the like. Although radiant furnace reactors are preferred, any high severity steam cracking system known to those of ordinary skill in the art may be employed.

Essential to the present invention is integration of the stream cracking process with the deep catalytic cracking process by recycling at least a portion of the effluent from the deep catalytic cracking process to the steam cracking process. A particularly advantageous integration according to the present invention comprises recycling one or more of the ethane-rich, propane-rich and/or $C_4$ hydrocarbon-rich recycle streams (described hereinbelow) from an olefin purification system located downstream of the deep catalytic cracking unit to the steam cracking unit.

Optionally, the recycle feedstocks to the steam cracking unit may be supplemented with a variety of other relatively light hydrocarbon feedstocks such as gas oils, naphthas, butane, propane, ethane or mixtures thereof. The hydrocarbon feed to the steam cracker can be in the liquid or vapor phase or may comprise a mixed liquid-vapor phase. The hydrocarbon is normally in the vapor phase in the reaction zone. The feed will generally be preheated in a preheat zone from about ambient temperature, e.g., 70° to 80° F. to an intermediate temperature. The preheated feed is then introduced into a convection zone of a pyrolysis furnace to further preheat the feed to a temperature below that at which significant reaction takes place, e.g., 1100° to 1300° F. During the convection zone preheating step, depending on the boiling range of the feed, the feed may be partially or completely vaporized. Steam is generally added to the feed prior to the feed being introduced to the radiant reaction zone of the pyrolysis furnace. The steam functions to maintain low hydrocarbon partial pressure in the radiant reaction zone. The feed is then cracked at very high temperatures, e.g., up to about 1650° F., in the radiant reaction zone of the pyrolysis furnace.

Typical operating conditions comprise an inlet temperature to the radiant heating section of the furnace ranging from about 1100° to about 1300° F. and an outlet temperature ranging from about 1500° to about 1650° F. The feed rate is such that the velocity through the radiant coils ranges from about 300 to about 800 feet per second, based on the total flow of steam and hydrocarbon. Steam is typically employed in amounts to provide a steam to feed weight ratio ranging from about 0.1 to about 2.0. The residence time of the feed in the radiant section of the cracking coil generally ranges from about 0.1 to about 1 second.

In order to prevent production of large amounts of undesirable by-products and in order to prevent severe coking, it is desirable to cool rapidly the effluent product gases issuing from the radiant zone from an exit temperature of from about 1500° to about 1650° F. to a temperature at which the cracking reactions substantially stop. This can be accomplished by rapidly cooling the effluent, such as in a suitable heat exchange apparatus or by direct quenching, by from about 100° to about 600° F. The cooling step is carried out very rapidly after the effluent leaves the radiant section of the furnace, i.e., about 1 to 30 milliseconds. See generally, e.g., Hallee et al., U.S. Pat. No. 3,407,789, and Woebcke, U.S. Pat. No. 3,910,347.

Integrating the steam cracking and deep catalytic cracking processes in the manner of the present invention, surprisingly provides a significantly improved degree of olefin product selectivity. The steam cracking is effective in utilizing $C_2$-$C_4$ paraffin-containing feedstocks and emphasizes the production of ethylene and propylene, while the deep catalytic cracking process provides significant propylene and butylene yields with moderate ethylene yields. Thus, where additional ethylene is required, all or a portion of the $C_2$-$C_4$ effluent from the deep catalytic cracking process may be recycled through the steam cracking process to provide additional ethylene. Alternatively, all or a portion of the paraffinic content of the $C_2$-$C_4$ effluent from the deep catalytic cracking process may be separated and recycled to the steam cracking process.

Another useful process component of the integrated process of the present invention is olefins purification. Olefins purification from hydrocarbon containing streams, such as from steam cracking plant effluents, is well known to those skilled in the art. Typically, the gaseous effluent is first passed through an atmospheric fractionator, then through a compression system, and then chilled and passed through a series of pressurized fractionators to separate the effluent into streams rich in its component parts, e.g., hydrogen, methane, ethane, propane, ethylene, propylene, and mixed $C_4$ hydrocarbon streams as is known to those of ordinary skill in the art. Conventional fractionation units are described in Roberts, U.S. Pat. No. 2,582,068; Rowles et al., U.S. Pat. Nos. 4,002,042, 4,270,940, 4,519,826, and 4,732,598; and Gazzi, U.S. Pat. No. 4,657,571. See also, Kaiser et al., "Hydrocarbon Processing," Nov. 1988, pp. 57–61. The streams rich in ethane and propane may conveniently be recycled to the steam cracker as described hereinabove.

Especially suitable for use herein are the cryogenic separation processes described in Mc Cue et al., U.S. Pat. Nos. 4,900,347 and 5,035,732. These processes employ serially connected dephlegmators upstream of serially connected demethanizers and deethanizers to cryogenically separate the gaseous mixtures.

In an especially preferred embodiment the olefins purification process comprises a compression system and a cryogenic separation process for recovering a plurality of component effluent streams comprising one or more of an ethane-rich stream, a propane-rich stream, an ethylene-rich stream, a propylene-rich stream, a mixed $C_4$ hydrocarbon-rich stream, and a gasoline-rich stream from the mixed olefin-containing effluent, wherein the cryogenic separation process comprises (A) introducing the mixed olefin containing-effluent into a dephlegmation or separation zone operating at cryogenic temperatures; (B) dephlegmating or separating the mixed olefin-containing effluent into a primary methane-rich gas stream and a primary liquid condensate stream rich in $C_2^+$ hydrocarbon components and containing a minor amount of methane; (C) separating the primary liquid condensate stream in a moderately low cryogenic temperature primary demethanizer unit into a $C_2^+$ liquid bottoms stream and an intermediate methane-rich overhead vapor stream; (D) separating the intermediate methane-rich overhead vapor stream in an ultra low cryogenic temperature final demethanizer into an ethylene-rich hydrocarbon product stream and a final demethanizer ultra-low temperature vapor stream; and (E) separating the $C_2^+$ liquid bottoms stream in at least one downstream fractionator into effluent streams comprising one or more of an ethane-rich stream, a propane-rich stream, a propylene-rich stream, a $C_4$ hydrocarbon-rich stream and a gasoline-rich stream.

A disproportionation (DP) or metathesis process step may be added to the process of the present invention, preferably downstream of the olefins purification process, in order to provide further surprising flexibility in the process product selectivity. Disproportionation or metathesis is a reaction in which one or more olefinic compounds are transformed into other olefins of different molecular weights. The disproportionation of an olefin with itself to produce an olefin of a higher molecular weight and an olefin of a lower molecular weight can also be referred to as self-disproportionation. For example, propylene can be self-disproportionated to ethylene and cis-2-butene, and trans-2-butene. Another type of disproportionation involves cross-disproportionation of two different olefins to form still other olefins. An example would be the cross-disproportionation of ethylene and 2-butenes to produce propylene. Although any of the known olefin disproportionation processes are contemplated herein, the cross-disproportionation reaction between ethylene and butylenes, and self-disproportionation reaction of propylene are particularly useful in the practice of the present invention.

The disproportionation equilibrium reactions between ethylene, propylene and the normal butenes are well known to those of ordinary skill in the art and any particular reaction process may be employed in the practice of the present invention. The general equilibrium reactions are shown below:

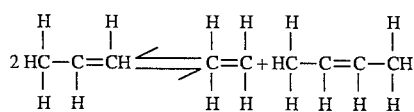

Many catalysts have been developed in the art to effect olefin disproportionation reactions. For example, those catalysts comprising inorganic oxides containing a catalytic amount of a metal or metal oxide have been employed widely for continuous, fixed bed conversion of olefins. A suitable catalyst comprising a silica support and an oxide of tungsten is described in Drake et al., U.S. Pat. No. 4,575,575, although any catalyst known to those skilled in the art may be employed. Still other catalysts can be found in Hatch and Matar, "From Hydrocarbons to Petrochemicals," Gulf Publishing Co., 1981, p. 121, Table 9–5.

The disproportionation reaction temperature can vary depending upon the catalyst and feed(s) employed and upon the desired reaction products. Typically the disproportionation is carried out at a temperature in the range of from about 0° to about 600° C. Further, for good conversion in relatively short reaction times, temperatures of from about 20° to about 500° C. are employed.

The disproportionation reaction can be carried out by contacting the olefins to be disproportionated with the catalyst in the liquid phase or the gas phase depending on the structure and molecular weight of the olefin. Pressure during the disproportionation reaction can vary between wide limits. For example, pressures between 0.1 and 500 atmospheres are suitable, although preferred pressures are between about 1 and 40 atmospheres because good conversions are obtained with readily available equipment.

If the reaction is carried out in the liquid phase, solvents or diluents for the reactants can be used. Aliphatic saturated hydrocarbons, e.g., pentanes, hexanes, cyclohexane and dodecane; and aromatic hydrocarbons such as benzene and toluene, are suitable. If the reaction is carried out in the gaseous phase, diluents such as saturated aliphatic hydrocarbons, for example, methane, ethane, and/or substantially inert gases, e.g., nitrogen, argon, can be present. Preferably, for high product yield, the disproportionation reaction is effected in the absence of significant amounts of deactivating materials such as water and oxygen.

The contact time needed to obtain a reasonable yield of disproportionation products depends upon several factors such as the activity of the catalyst, reaction temperature, reaction pressure and structure of the olefinic compound(s) to be disproportionated. The length of time during which the olefinic compounds to be disproportionated are contacted with the catalyst can conveniently vary between 0.1 second and 24 hours although longer and shorter contact times can be used. Preferably, for efficient use of reactor equipment, times of from about 1 second to about 1 hour are used.

The disproportionation process can be effected batchwise or continuously with fixed catalyst beds, slurried catalyst, fluidized beds, or by using any other convenient contacting techniques. These are well known to those of ordinary skill in the art.

The present invention also provides for further processing of the $C_4$ hydrocarbons. A variety of $C_4$ hydrocarbon processing techniques are contemplated by the present invention. All or a portion of the mixed $C_4$ stream may be selectively or totally hydrogenated and returned to the steam cracking unit. The mixed $C_4$ hydrocarbons may be separated and employed in polymerization processes or other downstream applications. Further, a portion of the isobutylene and isobutane may be removed by conventional fractionation and returned to the steam cracking furnace while the normal $C_4$ olefinic components are sent to the disproportionation zone.

A particularly useful $C_4$ hydrocarbon processing technique comprises a methyl tertiary butyl ether synthesis step which can be carried out in a number of ways well known to those skilled in the art. The synthesis of methyl tertiary butyl ether (MTBE) from isobutylene and methanol is a process which is well known to those of ordinary skill in the art and any particular synthesis process may be employed in the practice of the present invention. The general reaction scheme is set forth below.

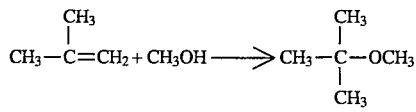

Typically, the synthesis step is carried out at mild temperatures, in the liquid phase, in the presence of a sulfonated polystyrene resin. See, Hatch and Matar, "From Hydrocarbons to Petrochemicals," Gulf Publishing Co., 1981, pp. 128–29. However, a mixed phase reaction may also be employed if desired.

The MTBE synthesis reaction usually employs an acid type ion exchange resin, such as a high molecular weight carbonaceous material containing sulfonate groups —$SO_3H$. Sulfonated resins of various types are available such as the sulfonated coals, phenol formaldehyde resins reacted with sulfuric acid, sulfonated resinous polymers of cumarone-indene with cyclopentadiene, strongly acidic cationic exchange resins such as sulfonated divinylbenzene polystyrene copolymers, and others, under various commercial names. The catalyst can be employed in a particulate solid form with sizes ranging from about 10 to about 50 U.S. sieve employing from about 0.5 to about 50 percent dry weight of catalyst relative to liquid content of the reactor. A fixed bed of particulate solid ion exchange resin catalyst, e.g., such as Amberlyst™ 15 from Rohm & Haas Co., or Dowex™ M31 or M32 from Dow Chemical Co., may be employed. The same catalyst may also be employed in tubular reactors or supported in bags or other devices which permit catalytic distillation to be practiced in the reactor.

The reaction of the isobutylene with methanol can be carried out under any suitable reaction conditions. The mole ratio of methanol to isobutylene generally is in the range of from about 0.05 to about 10, preferably from about 0.1 to about 5, and still more usually about 1 to 1, at a temperature in the range of from about 60° F. to about 300° F., more usually from about 100° F. to about 250° F., employing a pressure sufficient to maintain the reactants substantially in the liquid state, typically in the range of from about 80 to about 400 psig. However, mixed phase reactions are also contemplated by the present invention. The liquid hourly space velocity, volume of feed per volume of catalyst per hour, is preferably from about 0.5 to about 10.

More specific processes of MTBE synthesis are described in Childs, U.S. Pat. No. 4,440,963, Wentzheimer et al., U.S. Pat. No. 4,198,530, Masilamani et al., U.S. Pat. No. 4,792,639, Smith, Jr. et al., U.S. Pat. No. 4,950,803, Lee, U.S. Pat. No. 3,946,450 and Leum et al., U.S. Pat. No. 2,480,940.

In an alternative embodiment the mixed $C_4$ hydrocarbons are further processed in a processing zone comprising one or more of the following process steps, in any sequence: butadiene hydrogenation, MTBE synthesis, paraffin/olefin separation and skeletal isomerization with recycle of the skeletal isomerization effluent to the MTBE synthesis or butadiene hydrogenation unit. A particularly preferred $C_4$ hydrocarbon processing embodiment to produce MTBE is described more fully in commonly assigned U.S. Pat. No. application Ser. No. 08/042,477, filed Apr. 2, 1993.

The butadiene hydrogenation step may include a selective hydrogenation process to catalytically convert the butadienes and acetylenes in the mixed $C_4$ hydrocarbon-rich stream to butenes as is known to those of ordinary skill in the art. Particularly advantageous in the practice of the present invention is a butadiene hydrogenation step which comprises hydroisomerization to hydrogenate substantially all of the butadienes and acetylenes in the mixed $C_4$ hydrocarbon-rich stream to butenes and to convert at least a portion of the butene-1 in the mixed $C_4$ hydrocarbon-rich stream to butene-2 components.

Hydroisomerization is a process which is well known to those of ordinary skill in the art and any particular hydroisomerization process may be employed. Typically, the hydroisomerization step is carried out in the presence of a catalyst comprising at least one hydrogenating metal and a moderately acidic carrier. A preferred catalyst can comprise a Group VIII metal, such as platinum, palladium and/or nickel, on a microporous crystalline silicate, such as a mordenite with a surface area of from 100 to 800 $m^2/g$.

Suitable hydroisomerization conditions may include a temperature of from about 40° to about 400° C., a pressure of from about 1 to about 100 bar and a space velocity of from about 0.5 to about 20 kg hydrocarbon feed/kg catalyst hour. Preferred conditions are a mixed phase process at a temperature of from about 40° to about 150° C., a pressure of from about 10 to about 40 bar and a space velocity of from about 1 to about 15 kg feed/kg catalyst hour. See, e.g., Grandvallet et al., U.S. Pat. No. 5,023,389.

The paraffin/olefin separation step can be carried out by a wide variety of separation processes known to those skilled in the art, including, but not limited to, extractive distillation, selective membrane separation and/or molecular sieve separation. Particularly suitable for use in the practice of the present invention is an extractive distillation step to remove paraffins and $C_3$ components from the $C_4$ olefins remaining in the by-product stream of the MTBE synthesis unit.

Extractive distillation is also a well known process, and has been employed in the past to separate butadienes from $C_4$ feedstreams, as well as other separations such as separating MTBE from cyclopentane. See, e.g., Berg, U.S. Pat. No. 4,661,209. Extractive distillation generally refers to processes where a higher boiling selective solvent is added to alter the relative volatilities of the components in the feed mixture. See, generally, Perry and Chilton, "Chemical Engineers' Handbook," McGraw Hill, 5th ed., 1973, pp. 13–43 to 13–48.

A wide variety of solvents may be employed in the extractive distillation step of the present invention, including, but not limited to, tetrahydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing. Especially preferred is acetonitrile. Further, it is contemplated by the present invention that these solvents may also be employed with a water diluent.

The solvent is typically introduced near the top of the absorber tower of the extractive distillation unit, usually a few plates from the top, and flows downward until it reaches the stillpot or reboiler. Its presence on each plate of the distillation column alters the relative volatility of the close boiling compounds to make the separation on each plate greater than would be possible without the solvent and thus requires either fewer plates to effect the same separation, makes possible a greater degree of separation with the same number of plates and/or makes possible separations which could not be achieved with conventional distillation.

Skeletal isomerization, as practiced in the present invention, is a process by which the 2-butenes, cis-2-butene and trans-2-butene, are converted to isobutylene, and the 1-butene is isomerized to a 2-butene which can then be further isomerized to isobutylene. Skeletal isomerization of olefins is known to be conducted by contacting unbranched olefins with acidic catalysts at pressures near atmospheric and temperatures ranging from about 600° to 1100° F. The skeletal isomerization of olefins is well known to be limited by the thermodynamic equilibrium of reacting species. Useful catalysts and processes are described in the patent literature, inter alia, Smith, Jr., U.S. Pat. No. 4,482,775, Sun, U.S. Pat. No. 4,778,943, Schwerdtel et al., U.S. Pat. No. 4,548,913, Del Rossi et al., U.S. Pat. No. 5,107,047 and Chih-Cheng, et al., EP 0 508 008.

The process steps of the present invention can be combined in any order as long as there is present a deep catalytic cracking process integrated with a steam cracking process. Preferably, an olefins purification process sequence is provided downstream of the deep catalytic cracking process to separate the combined effluents into streams rich in the component products. It is further preferred to employ a disproportionation step downstream of the deep catalytic cracking process and steam cracking process. Additionally, a $C_4$ hydrocarbon processing sequence may be employed to convert the isobutylenes to methyl tertiary butyl ether product, where desired.

DESCRIPTION OF THE PREFERRED EMBODIMENTS

In an embodiment of the present invention, referring to FIG. 1, a relatively heavy hydrocarbon feedstock, such as a vacuum gas oil boiling from 350° C. to 540° C. in a line 2, is fed to a deep catalytic cracking reaction zone 4. In the deep catalytic cracking zone, the feed is cracked over a pentasil shape selective molecular sieve supported on kaolinite at a temperature of about 580° C., a weight hourly space velocity of about 1, a catalyst to oil ratio of about 5 and steam to hydrocarbon ratio of about 0.3. The effluent from the deep catalytic cracking zone 4, in a line 6, contains as its major components: cracked gas, ethylene, propylene, butylenes, and heavier components.

Concurrently, a relatively light hydrocarbon feed, such as gaseous propane, ethane, butane or mixtures thereof, in a line 8 is fed along with recycle ethane, propane and $C_4$ paraffins in lines 62, 60 and 58, respectively, as described hereinbelow, to a steam cracking zone 10. The steam cracking zone 10 is preferably a tubular radiant heated pyrolysis furnace operating at an inlet temperature to the radiant heating section of the furnace of about 1150° F. to about 1275° F. and an outlet temperature of from about 1550° to about 1650° F., a velocity through the radiant coils of from about 300 to about 800 feet per second, based on the total flow of steam and hydrocarbon and steam in an amount to provide a steam to feed weight ratio of from about 0.2 to about 1.0. The residence time of the feed in the radiant section of the cracking coil is about 0.2 seconds. The effluent from the steam cracking zone 10 in a line 12 comprises mainly hydrogen, methane, ethane, ethylene, propane, propylene and heavier hydrocarbons.

The effluents, in lines 6 and 12 from the two cracking zones, 4 and 10, respectively, are cooled (not shown) and then combined in a line 7 and directed to an atmospheric fraction tower 91 wherein most of the diesel and fuel oil fractions are separated and removed in a line 99 while the lighter hydrocarbons are sent via a line 14 to a compression system 16 which operates to increase the pressure of the combined effluent to from about 350 psig to about 520 psig. Remaining diesel and fuel oil is separated and recycled from the compression system 16 to the atmospheric tower 91 via a line 93. The compressed effluent in a line 18 is then directed to a cryogenic chilling train 20 where the gas mixture is chilled to from about −185° F. to about −235° F., preferably comprising serially connected dephlegmators, as described in the above-mentioned patents to McCue et al., to separate the effluent into hydrogen gas in a line 22, primarily methane in a line 24 and heavier components which are withdrawn from the cryogenic chilling train 20 in a line 26. Conventional heat exchangers, liquid/vapor separation vessels and fractionation towers may also be employed to separate hydrogen and fuel gas from heavier hydrocarbons. Alternatively, in embodiments where the hydrogen and methane components are relatively low, all or a portion of the effluent from the compressor in a line 14 may by-pass the chilling train 20 by the provision of a by-pass line 28. Additionally, gasoline removed in the compression system 16 may be directed to the pressurized fractionation system 30 via the by-pass line 28.

The effluent from the chilling train 20 in a line 26 is then further separated in the pressurized fractionation system 30, which typically includes serially connected towers comprising demethanizer(s), deethanizer(s), depropanizer(s), etc., to produce streams which are rich in ethylene in a line 34, propylene in a line 40, gasoline in a line 46, mixed $C_4$ hydrocarbon components in a line 48, propane in a line 60 and ethane in a line 62. Additionally, hydrogen may be added to the fractionation zone 30 through a line 32 for conversion of $C_2$ and $C_3$ acetylenes to olefins and paraffins.

Either all or a portion of the ethylene and normal butylenes or propylene, in streams 34, 48 and 40, respectively, can be fed to a disproportionation zone 38, via lines 36, 97 and 42, respectively, to produce additional propylene in the case of ethylene and n-butylenes, or n-butylenes and ethylene in the case of propylene. The product effluent from the disproportionation zone 38 in a line 44 is then conveniently recycled to the cryogenic chilling chain 20 via a line 47 or to fractionation system 30 via a line 45 for subsequent separation into its respective components.

In this manner, where the feed to the disproportionation zone 38 is ethylene and n-butylenes, additional propylene is able to be separated in the fractionation zone 30 and recovered in a product stream 41. On the other hand, where the feed to the disproportionation zone 38 is propylene, additional n-butylenes and ethylene can be separated in the fractionation zone 30 and recovered as product ethylene in a product stream 35 and as mixed $C_4$ hydrocarbons in a stream 48.

Thus, the disproportionation zone 38 can be operated in a flexible mode to produce either propylene from ethylene and normal butylenes or to produce ethylene and normal butylenes from propylene. When producing additional propylene, all or a portion of the normal butylenes via a line 97 from the $C_4$ hydrocarbon processing zone 50 and all or a portion of ethylene from line 34 via a line 35 can be fed to the disproportionation zone 38. In the other mode of operation, producing additional ethylene and normal butylenes, all or a portion of the propylene via a line 42 is fed to the disproportionation zone 38.

All of the olefin feeds to the disproportionation zone 38 are free of, or substantially free of, contaminants such as water, sulfur compounds and other impurities by appropriate treating (not shown) of the respective olefin stream.

The mixed $C_4$ hydrocarbon-rich stream recovered from the fractionation zone 30 in a line 48 is directed to a $C_4$ processing zone 50. Where it is not desired to produce methyl tertiary butyl ether, the mixed $C_4$ hydrocarbon-rich stream may be recovered directly and separated into component parts as is known to those skilled in the art (not shown), or, may be recycled, with or without hydrogenation, to steam cracking unit 10 for cracking to ethylene and propylene (not shown).

Figure 2:
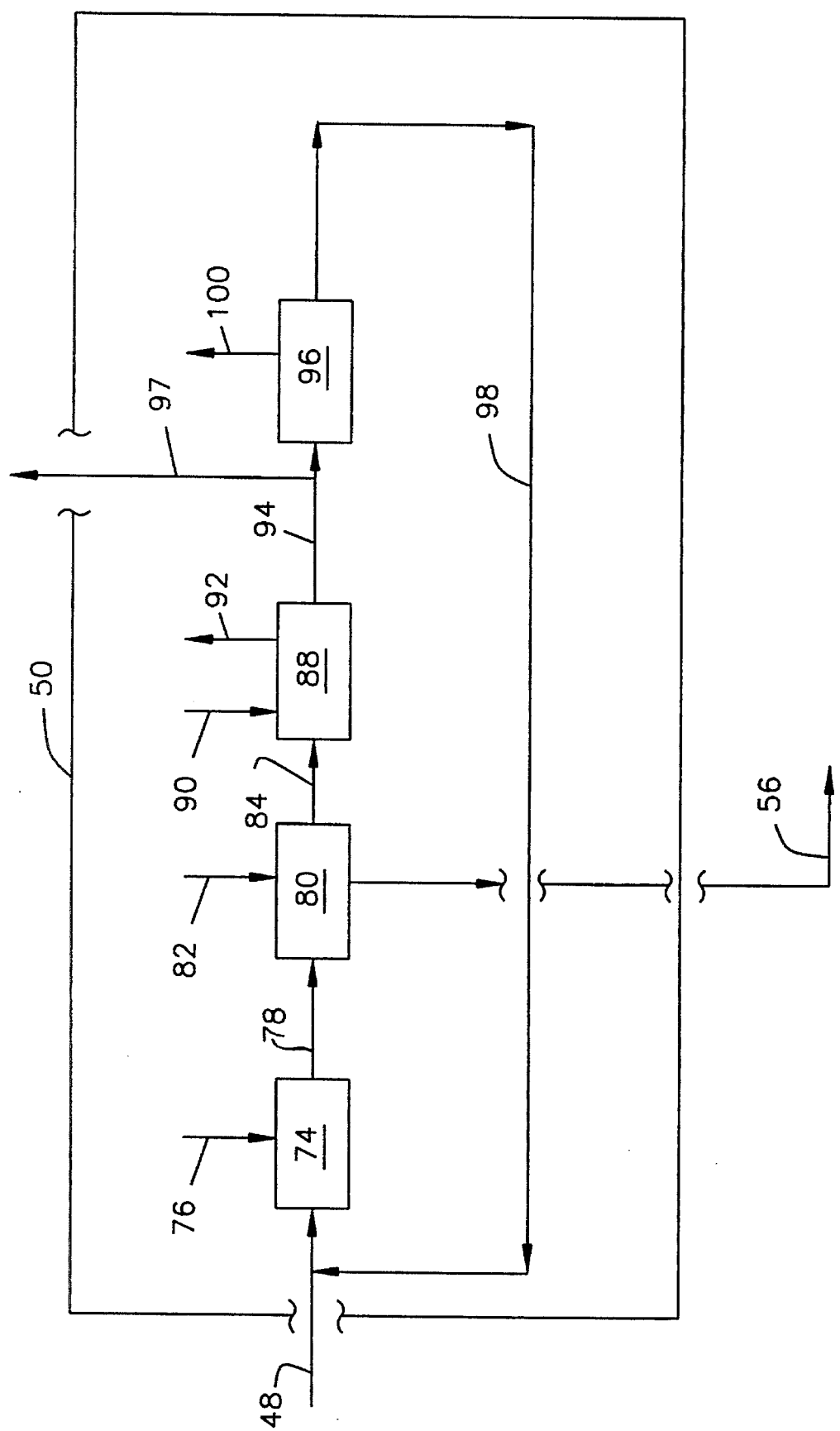
FIG. 2 depicts in flow chart form a preferred $C_4$ processing zone configuration for use in the practice of the present invention.

In a preferred embodiment, where it is desired to produce methyl tertiary butyl ether, as best seen in FIG. 2, the mixed $C_4$ hydrocarbon-rich stream in a line 48 is directed into $C_4$ processing zone 50 and first fed to a hydroisomerization unit 74. Alternatively, the hydroisomerization unit 74 can comprise any butadiene hydrogenation unit known to those of ordinary skill in the art which converts butadienes and acetylenes to butenes, such as a hydroisomerization unit or selective hydrogenation unit. Preferred is a hydroisomerization unit which in addition to converting butadiene to butenes also isomerizes at least a portion of the butene-1 component to the butene-2 components.

The hydroisomerization unit 74 is fed with hydrogen via a line 76. The mixed $C_4$ hydrocarbon-rich stream 48 typically comprises all of the $C_4$ isomers (acetylenes, dienes, olefins and paraffins), and small quantities of $C_3$ and $C_5$ hydrocarbons. The $C_4$ isomers are as follows: ethyl acetylene, vinyl acetylene, 1,3-butadiene, 1,2-butadiene, isobutylene, 1-butene, cis-2-butene, trans-2-butene, isobutane and n-butane. The actual composition of the mixed $C_4$ hydrocarbon-rich stream 48 may vary considerably and will further differ if an optional butadiene extraction unit (not shown) is employed upstream to recover butadiene from the mixed $C_4$ hydrocarbon-rich stream 48.

In the hydroisomerization unit 74, most of the acetylenes and dienes contained in the mixed $C_4$ hydrocarbon-rich stream 48 are catalytically converted to butenes and at least a portion of the 1-butene contained in the mixed $C_4$ hydrocarbon-rich stream 48 is catalytically converted to the 2-butenes, i.e., cis-2-butene and trans-2-butene, in the presence of hydrogen supplied via a line 76.

The hydroisomerized effluent stream 78 from the hydroisomerization unit 74 substantially comprising isobutylene, cis-2-butene, trans-2-butene, isobutane, n-butane, 1-butene and $C_3$ and $C_5$ components is directed to a methyl tertiary butyl ether synthesis unit 80.

In the methyl tertiary butyl ether synthesis unit 80, at least a portion of the isobutylene contained in the hydroisomerized effluent 78 is reacted with methanol, added to the synthesis unit 80 via a line 82, to produce methyl tertiary butyl ether.

The resultant product methyl tertiary butyl ether, along with the $C_5$ and heavier components, is withdrawn from the methyl tertiary butyl ether synthesis unit through a product line 56 by fractionation (not shown), as is well known to those skilled in the art. The remaining components from the methyl tertiary butyl ether feed stream, the cis-2-butene, trans-2-butene, isobutane, n-butane, 1-butene and $C_3$ components are then directed through a by-product line 84 to an extractive distillation unit 88. The extractive distillation unit is equipped with a solvent feed line 90, preferably located near the top of the absorber tower of the extractive distillation unit (not shown).

The light compounds, $C_3$ and lighter boiling hydrocarbons, as well as the $C_4$ paraffins, isobutane and n-butane, are thereby removed from the top of the stripper (not shown) of the extractive distillation unit 88 through a line 92. These light compounds and $C_4$ paraffins may be removed from the solvent and recycled to the steam cracking unit 10 via a line 58 (see FIG. 1). Accordingly, it is also contemplated by the present invention to recycle the recovered solvent within the extractive distillation unit 88. The bottoms from the extractive distillation absorber are directed to a stripper (not shown) wherein the cis-2-butene, trans-2-butene and unconverted 1-butene are recovered from the overhead of the stripper, withdrawn through a line 94 and fed to the skeletal isomerization unit 96. Solvent from the stripper bottoms may also be recycled to the absorber.

Alternatively, where additional propylene is desired, all or a portion of the normal butenes in the line 94 may be withdrawn in a line 97 and directed to disproportionation zone 38 as described hereinabove.

In skeletal isomerization unit 96, at least a portion of the 2-butenes from the line 94 are converted to isobutylene with a small amount of light and heavy hydrocarbon by-products (gasoline). The effluent from the skeletal isomerization unit is then recycled in a line 98 to the hydroisomerization zone and then to the MTBE synthesis unit for conversion of the isobutylene to MTBE product. Further, the heavy hydrocarbon by-products (gasoline) can be withdrawn from the skeletal isomerization unit through a line 100.

Several alternate processing methods may also be employed in the $C_4$ processing zone 50. All or a portion of the mixed $C_4$ hydrocarbon-rich stream 48 may be selectively or totally hydrogenated and returned to steam cracking zone 10. In addition, all or a portion of the MTBE synthesis by-product effluent stream 84 may be returned to the steam cracking zone 10. A portion of the isobutylene and isobutane in hydrogenated $C_4$ hydrocarbon-rich stream 78 may be removed by conventional fractionation and returned to the steam cracking zone 10 together with $C_4$ paraffins from the stream 92 from the olefin-paraffin separation zone 88.

Returning to FIG. 1, propane and ethane recovered from the fractionation zone 30 are recycled, in lines 60 and 62, respectively, to combine with the $C_4$ recycle line 58 for return to the steam cracking zone 10.

The following examples illustrate the present invention. They are not to be construed to limit the scope of the appended claims in any manner whatsoever.

EXAMPLE 1

Typical yields from deep catalytic cracking (DCC) and steam cracking (SC) processes are reported below in Table 1. For comparative purposes, a typical yield for a fluid catalytic cracking (FCC) process is also reported.

TABLE 1

| Process Component | DCC | SC | FCC |
| --- | --- | --- | --- |
| $H_2$ | 0.3 | 0.8 | 0.3 |
| Dry Gas ($C_1$-$C_2$) | 12.6 | 48.7 | 3.9 |
| LPG ($C_3$-$C_4$) | 42.3 | 24.9 | 27.5 |
| Gasoline | 20.2 | 19.3 | 47.9 |
| Light Cycle Oil[a] | 7.9 | 4.7 | 8.4 |
| Decant Oil[b] | 7.3 | 1.6 | 5.9 |
| Coke | 9.4 | — | 6.1 |

[a] = 400–630° F.
[b] = 630° F.+
DCC = Deep Catalytic Cracking process
SC = Steam Cracking process
FCC = Fluid Catalytic Cracking process From Table 1 it can be seen that DCC is more effective in producing $C_3$-$C_4$ hydrocarbon components, SC is more effective in producing $C_1$-$C_2$ hydrocarbon components, while FCC is more effective in producing gasoline.

EXAMPLE 2

Typical light olefin yields for the process employing a 25,000 metric tons per annum deep catalytic cracking process, a disproportionation process and the methyl tertiary butyl ether synthesis process of FIG. 2 are reported below. For comparative purposes, a process without the disproportionation process is also reported.

TABLE 2

| Process Product[a] | A | B | Percent Increase |
| --- | --- | --- | --- |
| Ethylene | 61,388 | 129,250 | 110.5 |
| Propylene | 221,946 | 387,713 | 74.6 |
| MTBE | 214,595 | 279,249 | 30.1 |

A = Deep catalytic cracking and MTBE synthesis
B = Deep catalytic cracking, disproportionation and MTBE synthesis
MTBE = methyl tertiary butyl ether
[a] = in metric tons per annum Table 2 above shows the flexibility provided by including a disproportionation zone.

EXAMPLE 3

Typical steam cracking gas yields for ethane and propane feedstocks are reported below in Table 3.

TABLE 3

| Feedstock Conversion, % Components, weight % | Ethane 60 | Propane 93 |
| --- | --- | --- |
| $H_2$ | 4.33 | 1.55 |
| $CH_4$ | 3.17 | 22.85 |
| $C_2H_2$ | 0.20 | 0.77 |
| $C_2H_4$ | 40.82 | 4.54 |
| $C_2H_6$ | 46.67 | 38.55 |
| $C_3H_4$ | 0.08 | 0.91 |
| $C_3H_6$ | 1.80 | 13.52 |
| $C_3H_8$ | 0.06 | 6.55 |
| $C_4H_6$ | 0.40 | 2.70 |
| $C_4H_8$ | 0.49 | 0.54 |
| Other $C_4$'s | 0.14 | 0.01 |
| $C_{5+}$ | 1.84 | 7.51 |

EXAMPLES 4–9

Computer simulations of the processes according to FIGS. 3–8 were performed and are described below. The results of material balances for each of the processes are tabulated below in Table 4. In each of the FIGS. 3–8, the reference characters generally correspond to like reference characters in FIGS. 1 and 2, except in the 300, 400, 500, 600, 700, 800 and 900 series respectively.

COMPARATIVE EXAMPLE 4

Figure 3:
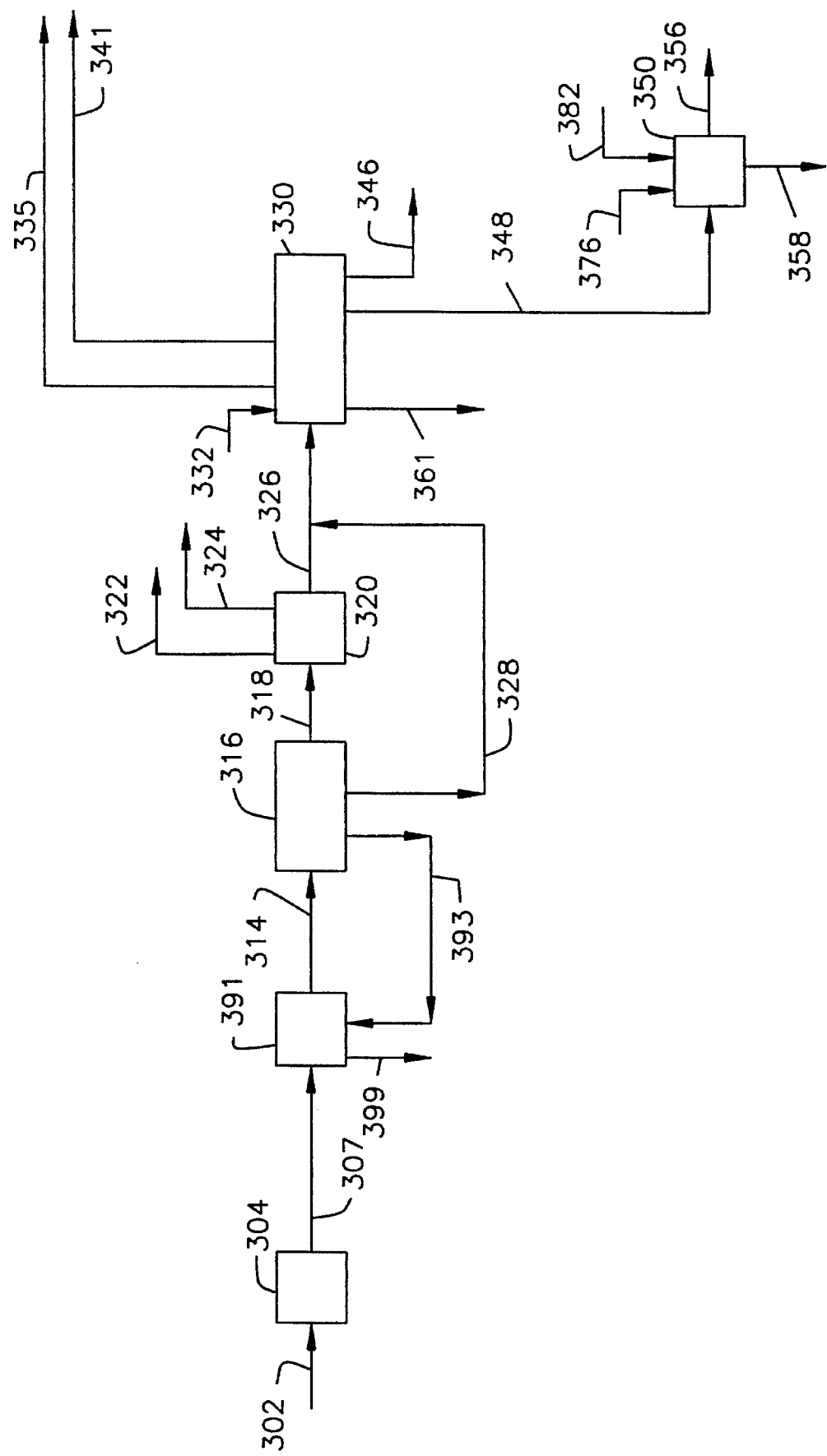
FIG. 3 depicts in flow chart form a comparative process which does not include an integrated steam cracking process step.

Referring to FIG. 3, which describes deep catalytic cracking of a gas oil without an integrated steam cracking step, 25000 barrels per stream day (BPSD) of a vacuum gas oil in a line 302 are fed to a deep catalytic cracking unit 304. The cracked effluent from the deep catalytic cracking unit comprising mostly cracked gas, ethylene, propylene, butylenes, light paraffins, gasoline, and diesel and fuel oils is directed to an atmospheric fractionator 391 via a line 307. In the atmospheric fractionator 391, diesel and fuel oils are removed via a line 399.

The effluent in a line 314 from the atmospheric fractionator 391 comprising mostly cracked gas, ethylene, propylene, butylenes, light paraffins, gasoline and remaining diesel and fuel oils are directed to a compression system 316. The compression system 316 preferably comprises a series of compressors and knock out drums and fractionation tower(s) (not shown) as is known to those skilled in the art. In the compression system 316, remaining diesel and fuel oils are removed and recycled to the atmospheric tower 391 via a recycle line 393. Additionally, gasoline removed in the compression system 316 is directed to the pressurized fractionation system 330 via a by-pass line 328.

The gaseous effluent from the compression system in a line 318 comprising mainly cracked gas, ethylene, propylene, butylenes and light paraffins are fed to chilling train 320 wherein hydrogen and methane are removed in lines 322 and 324, respectively. The remaining effluent in a line 326 comprising mainly ethylene, propylene, butylenes and light paraffins is combined with by-pass line 328 and fed to the pressurized fractionation unit 330 for separation into its component parts. Additionally, hydrogen is added via a line 332 for hydrogenation of $C_2$ and $C_3$ acetylenes to olefins and paraffins.

Ethylene and propylene are removed from the pressurized fractionation system 330 in product lines 335 and 341, respectively. Similarly, gasoline is recovered in product line 346. Ethane and propane are recovered and combined together in a line 361.

The $C_4$ hydrocarbons are removed in a line 348 and fed to a $C_4$ hydrocarbon processing zone 350. In the $C_4$ hydrocarbon processing zone 350 the butadienes are first selectively hydrogenated to butenes (not shown). The isobutylene in the mixed $C_4$ hydrocarbons is reacted with methanol from a line 382 to produce methyl tertiary butyl ether product in a line 356. The remaining $C_4$ olefins are further hydrogenated to butanes in a line 358 with hydrogen supplied to the $C_4$ hydrocarbon processing unit 350 via a line 376.

EXAMPLE 5

Figure 4:
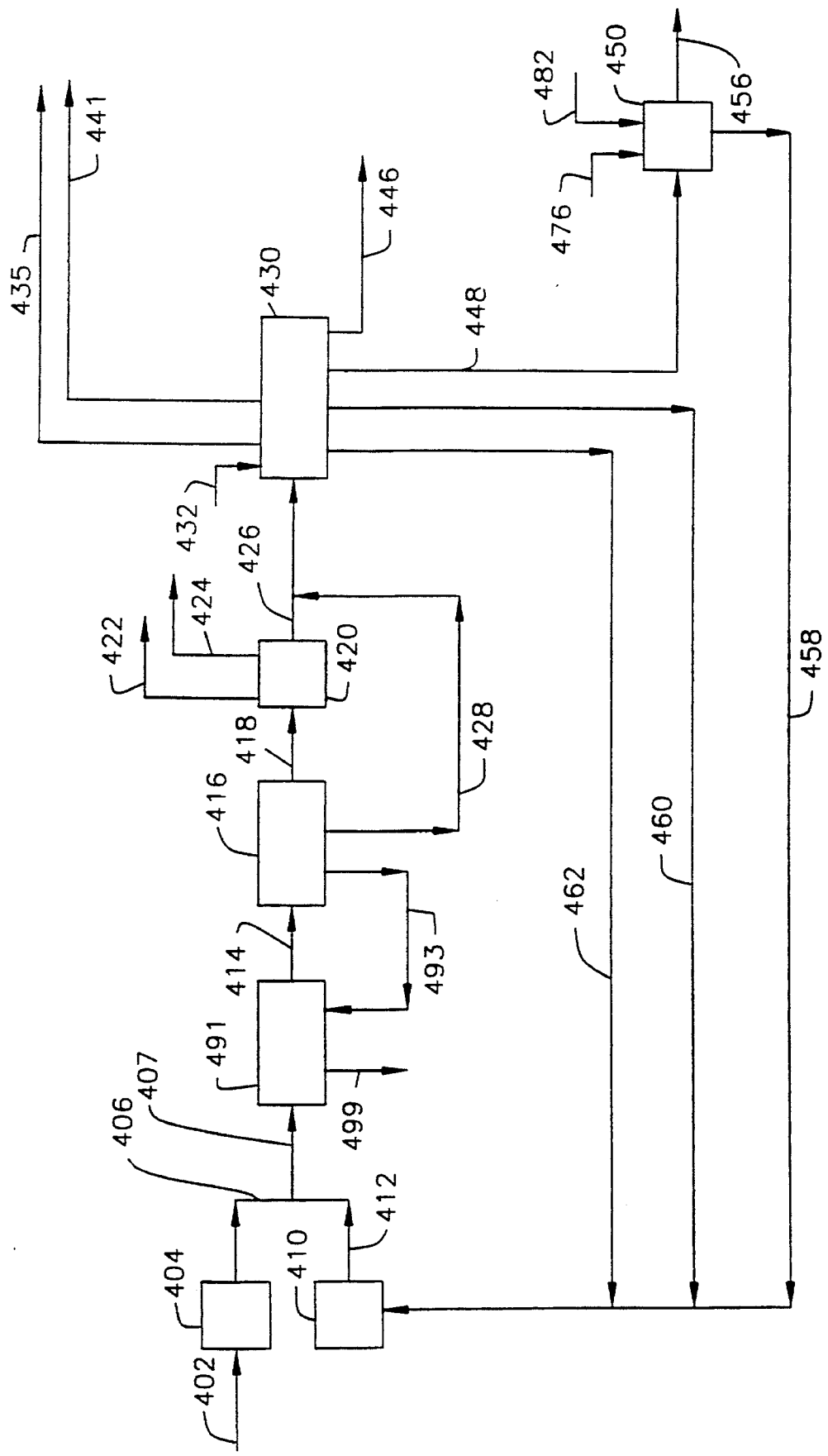
FIG. 4 depicts in flow chart form another embodiment of the present invention.

Referring to FIG. 4, which describes deep catalytic cracking integrated with steam cracking, 25000 BPSD of a vacuum gas oil in a line 402 are fed to a deep catalytic cracking unit 404. The cracked effluent from the deep catalytic cracking unit comprising mostly cracked gas, ethylene, propylene, butylenes, light paraffins, gasoline, and diesel and fuel oils in a line 406 is directed to an atmospheric fractionator 491 via a line 407. In the atmospheric fractionator 491, diesel and fuel oils are removed via a line 499.

The effluent from the atmospheric fractionator 491 in a line 414 comprising mostly cracked gas, ethylene, propylene, butylenes, light paraffins, gasoline and remaining diesel and fuel oils is directed to a compression system 416. The compression system 416 preferably comprises a series of compressors and knock out drums and fractionation tower(s) (not shown) as is known to those skilled in the art. In the compression system 416, remaining diesel and fuel oils are removed and recycled to the atmospheric tower 491 via a recycle line 493. Additionally, gasoline removed in the compression system 416 is directed to the pressurized fractionation system 430 via a by-pass line 428.

The effluent from the compression system in a line 418 comprising mainly cracked gas, ethylene, propylene, butylenes and light paraffins is fed to a chilling train 420 wherein hydrogen and methane are removed in lines 422 and 424, respectively. The remaining effluent in a line 426 comprising mainly ethylene, propylene, butylenes and light paraffins are combined with by-pass line 428 and fed to a pressurized fractionation unit 430 for separation into its component parts. Additionally, hydrogen is added via a line 432 for hydrogenation of $C_2$ and $C_3$ acetylenes to olefins and paraffins.

Ethylene and propylene are removed from pressurized fractionation system 430 in product lines 435 and 441, respectively. Similarly, gasoline is recovered in a product line 446. Ethane and propane are removed in lines 462 and 460, respectively, for recycle to the steam cracking unit 410. The $C_4$ hydrocarbons are removed in a line 448 and fed to a $C_4$ hydrocarbon processing zone 450.

In $C_4$ hydrocarbon processing zone 450 the butadienes are first selectively hydrogenated to butenes (not shown). The isobutylene in the $C_4$ hydrocarbons is reacted with methanol from a line 482 to produce methyl tertiary butyl ether product in a line 456. The remaining $C_4$ olefins are further hydrogenated to butanes and recycled in a line 458 to steam cracking unit 410. Hydrogen is supplied to the $C_4$ hydrocarbon processing unit 450 via a line 476.

The recycle propane, ethane and butanes in lines 460, 462 and 458 are directed to the steam cracking unit 410 for cracking to mainly ethylene and propylene. The effluent from the steam cracking unit 410 in a line 412 is combined with the effluent from the deep catalytic cracking unit 406 in a line 407 for further processing as described above.

EXAMPLE 6

Figure 5:
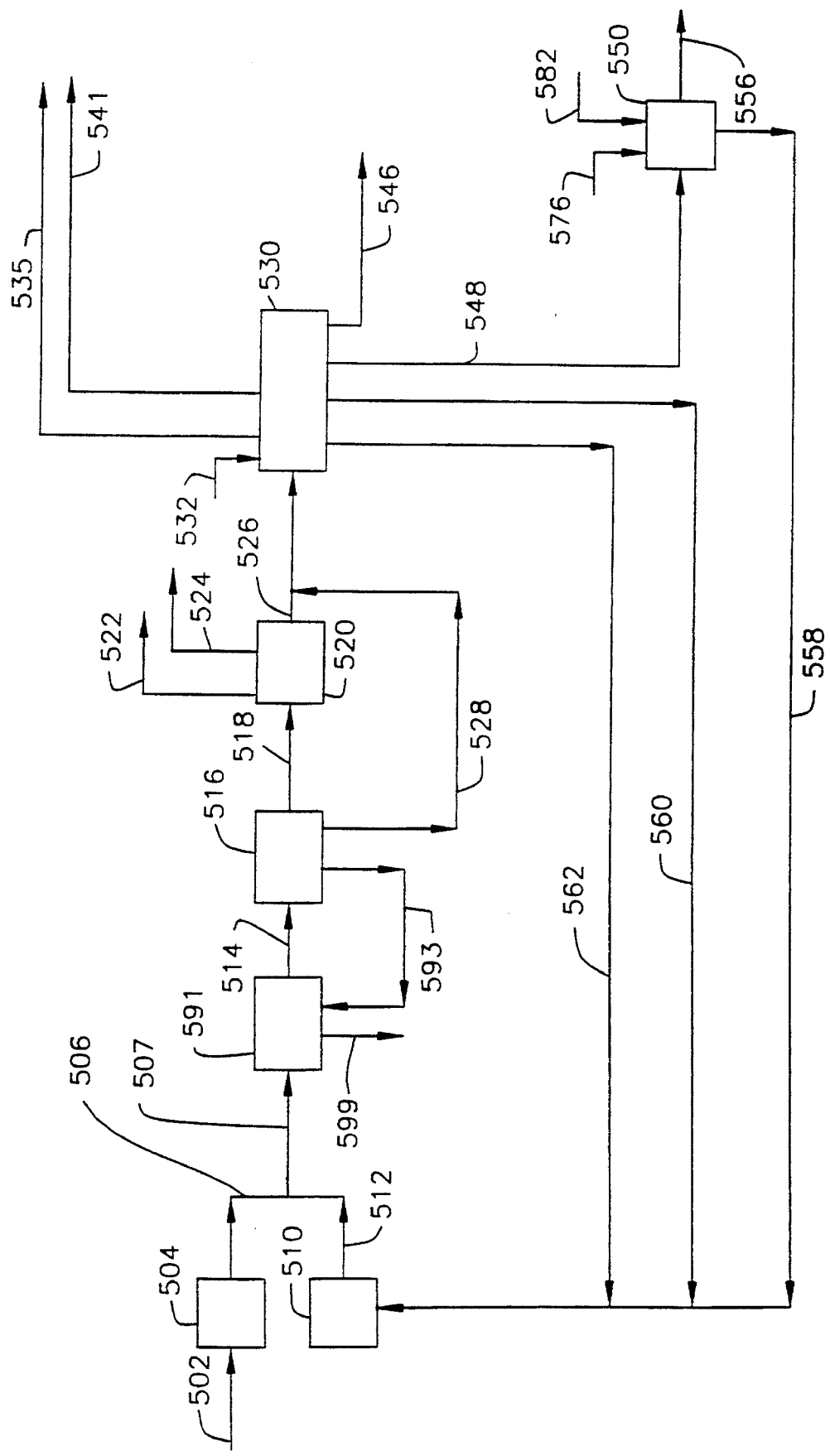
FIG. 5 depicts in flow chart form still another alternative embodiment of the present invention.

Referring to FIG. 5, which describes deep catalytic cracking integrated with steam cracking, skeletal isomerization and extractive distillation, 25000 BPSD of a vacuum gas oil in a line 502 are fed to a deep catalytic cracking unit 504. The cracked effluent from the deep catalytic cracking unit comprising mostly cracked gas, ethylene, propylene, butylenes, light paraffins, gasoline, and diesel and fuel oils in a line 506 is directed to a atmospheric fractionator 591 via a line 507. In the atmospheric fractionator 591, diesel and fuel oils are removed via a line 599.

The effluent from the atmospheric fractionator 591 in a line 514 comprising mostly cracked gas, ethylene, propylene, butylenes, light paraffins, gasoline and remaining diesel and fuel oils is directed to a compression system 516. The compression system 516 preferably comprises a series of compressors and knock out drums and fractionation tower(s) (not shown) as is known to those skilled in the art. In the compression system 516, remaining diesel and fuel oils are removed and recycled to the atmospheric tower 591 via a recycle line 593. Additionally, gasoline removed in the compression system 516 is directed to the pressurized fractionation system 530 via a by-pass line 528.

The effluent from the compression system in a line 518 comprising mainly cracked gas, ethylene, propylene, butylenes and light paraffins is fed to chilling train 520 wherein hydrogen and methane are removed in lines 522 and 524, respectively. The remaining effluent in a line 526 comprising mainly ethylene, propylene, butylenes and light paraffins are combined with gasoline in a by-pass line 528 and fed to pressurized fractionation unit 530 for separation into its component parts. Additionally, hydrogen is added via a line 532 for hydrogenation of $C_2$ and $C_3$ acetylenes to olefins and paraffins.

Ethylene and propylene are recovered from fractionation system 530 in product lines 535 and 541, respectively. Similarly, gasoline is recovered in a product line 546. Ethane and propane are removed in lines 562 and 560, respectively, for recycle to the steam cracking unit 510. The $C_4$ hydrocarbons are removed in a line 548 and fed to a $C_4$ hydrocarbon processing zone 550.

In $C_4$ hydrocarbon processing zone 550 the butadienes are hydrogenated to butenes and most of the 1-butene is hydroisomerized to 2-butenes (not shown). The isobutylene is then reacted with methanol from a line 582 to produce methyl tertiary butyl ether product in a line 556. The normal butenes are separated from the butanes via extractive distillation (not shown). The normal butenes are then directed to a skeletal isomerization reactor (not shown) where a portion of the normal butenes are converted to isobutylene. The effluent from the skeletal isomerization reactor is then recycled to the methyl tertiary butyl ether reactor for reaction of the additional isobutylene with methanol (not shown). The butanes removed in the extractive distillation unit are recycled in a line 558 to the steam cracking unit 510. Hydrogen is supplied to the $C_4$ hydrocarbon processing unit via a line 576.

The recycle propane, ethane and butanes in lines 560, 562 and 558, respectively, are directed to the steam cracking unit 510 for cracking to mainly ethylene and propylene. The effluent from the steam cracking unit 510 in a line 512 is combined with the effluent from the deep catalytic cracking unit 506 in a line 507 for further processing as described above.

EXAMPLE 7

Figure 6:
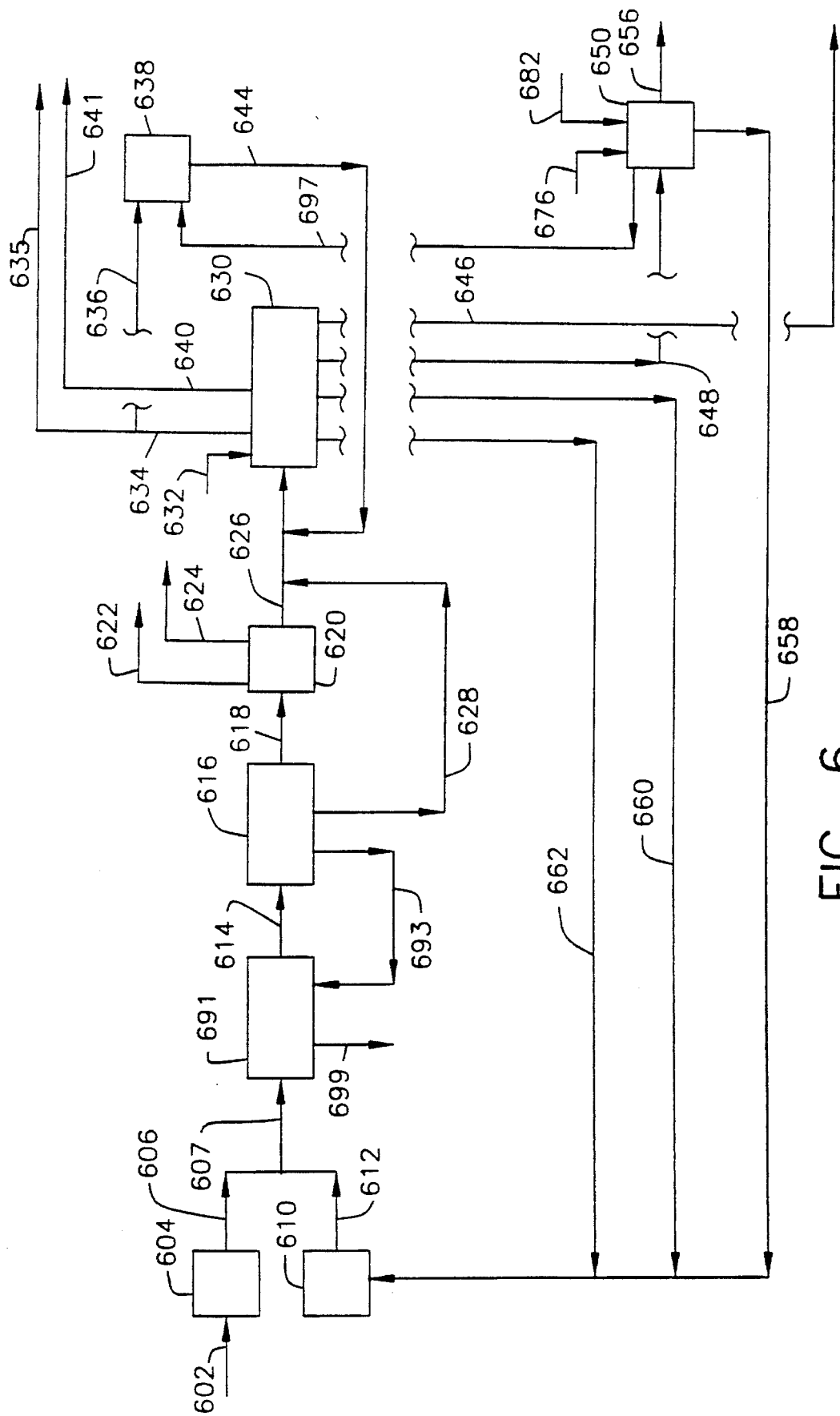
FIG. 6 depicts in flow chart form an embodiment of the present invention to increase propylene product.

Referring to FIG. 6, which describes deep catalytic cracking integrated with steam cracking and disproportionation for propylene production, 25000 BPSD of a vacuum gas oil in a line 602 are fed to a deep catalytic cracking unit 604. The cracked effluent from the deep catalytic cracking unit comprising mostly cracked gas, ethylene, propylene, butylenes, light paraffins, gasoline, and diesel and fuel oils in a line 606 is directed to an atmospheric fractionator 691 via a line 607. In the atmospheric fractionator 691, diesel and fuel oils are removed via a line 699.

The effluent from the atmospheric fractionator 691 in a line 614 comprising mostly cracked gas, ethylene, propylene, butylenes, light paraffins, gasoline and remaining diesel and fuel oils are directed to a compression system 616. The compression system 616 preferably comprises a series of compressors and knock out drums and fractionation tower(s) (not shown) as is known to those skilled in the art. In the compression system 616, remaining diesel and fuel oils are removed and recycled to the atmospheric tower 691 via a recycle line 693. Additionally, gasoline removed in the compression system 616 is directed to the pressurized fractionation system 630 via a by-pass line 628.

The effluent from the compression system in a line 618 comprising mainly cracked gas, ethylene, propylene, butylenes and light paraffins is fed to a chilling train 620 wherein hydrogen and methane are removed in lines 622 and 624, respectively. The remaining effluent in a line 626 comprising mainly ethylene, propylene, butylenes and light paraffins is combined with gasoline in a by-pass line 628 and fed to a pressurized fractionation unit 630 for separation into its component parts. Additionally, hydrogen is added via a line 632 for hydrogenation of $C_2$ and $C_3$ acetylenes to olefins and paraffins.

Ethylene is removed from pressurized fractionation system 630 in line 634. A portion of the ethylene is directed via a line 636 to a disproportionation unit 638 wherein it is disproportionated with butenes from a line 697 (described hereinbelow) to produce additional propylene. The effluent from the disproportionation unit 638 containing the additional propylene along with ethylene and butylenes is recycled to the pressurized fractionation system 630 via a line 644 for separation and recovery. The other portion of the ethylene in the line 634 is removed as product via a product line 635.

Propylene is recovered from fractionation system 630 via a product line 641. Similarly, gasoline is recovered in a product line 646. Ethane and propane are removed in lines 662 and 660, respectively, for recycle to the steam cracking unit 610. The $C_4$ hydrocarbons are removed in a line 648 and fed to a $C_4$ hydrocarbon processing zone 650.

In $C_4$ hydrocarbon processing zone 650 the butadienes are first selectively hydrogenated to butenes (not shown). The isobutylene in the mixed $C_4$ hydrocarbons is reacted with methanol from a line 682 to produce methyl tertiary butyl ether product in a line 656. The normal butenes are separated from the butanes (not shown) and directed via a line 697 to the disproportionation unit 638 for disproportionation with ethylene to produce additional propylene. The butanes are recycled in a line 658 to steam cracking unit 610. Hydrogen is supplied to the $C_4$ hydrocarbon processing unit via a line 676.

The recycle propane, ethane and butanes in lines 660, 662 and 658, respectively, are directed to the steam cracking unit 610 for cracking to mainly ethylene and propylene. The effluent from the steam cracking unit 610 in a line 612 is combined with the effluent from the deep catalytic cracking unit 606 in a line 607 for further processing as described above.

EXAMPLE 8

Figure 7:
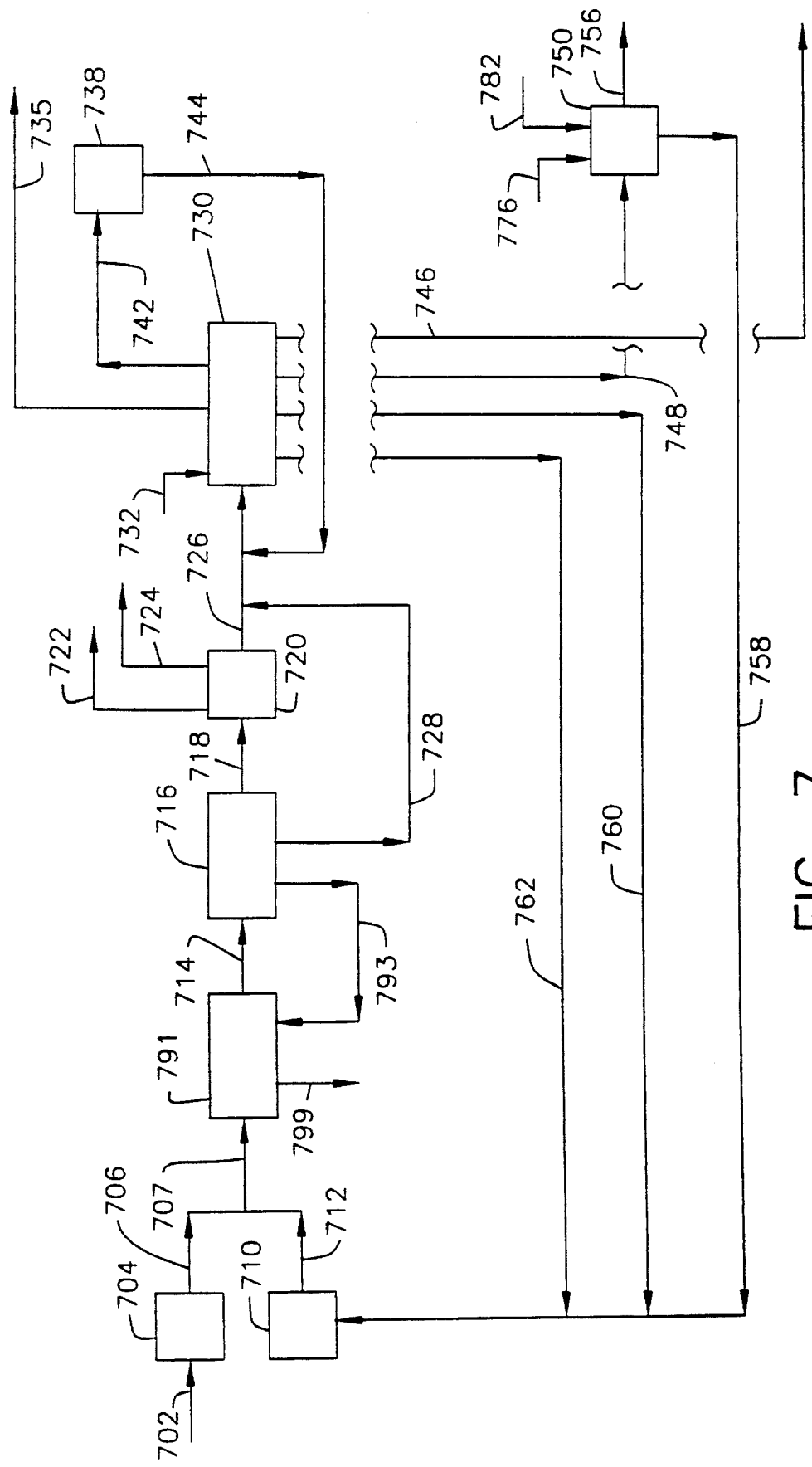
FIG. 7 depicts in flow chart form an embodiment of the present invention to increase methyl tertiary butyl ether product.

Referring to FIG. 7, which describes deep catalytic cracking integrated with steam cracking, extractive distillation, skeletal isomerization and disproportionation for ethylene and butylene production, 25000 BPSD of a vacuum gas oil in a line 702 are fed to a deep catalytic cracking unit 704. The cracked effluent from the deep catalytic cracking unit comprising mostly cracked gas, ethylene, propylene, butylenes, light paraffins, gasoline, and diesel and fuel oils in a line 706 is directed to an atmospheric fractionator 791 via a line 707. In the atmospheric fractionator 791, diesel and fuel oils are removed via a line 799.

The effluent from the atmospheric fractionator 791 in a line 714 comprising mostly cracked gas, ethylene, propylene, butylenes, light paraffins, gasoline and remaining diesel and fuel oils are directed to a compression system 716. The compression system 716 preferably comprises a series of compressors and knock out drums and fractionation tower(s) (not shown) as is known to those skilled in the art. In the compression system 716, remaining diesel and fuel oils are removed and recycled to the atmospheric tower 791 via a recycle line 793. Additionally, gasoline removed in the compression system 716 is directed to the pressurized fractionation system 730 via a by-pass line 728.

The effluent from the compression system in a line 718 comprising mainly cracked gas, ethylene, propylene, butylenes and light paraffins is fed to a chilling train 720 wherein hydrogen and methane are removed in lines 722 and 724, respectively. The remaining effluent in a line 726 comprising mainly ethylene, propylene, butylenes and light paraffins is combined with gasoline in a by-pass line 728 and fed to pressurized fractionation unit 730 for separation into its component parts. Additionally, hydrogen is added via a line 732 for hydrogenation of $C_2$ and $C_3$ acetylenes to olefins and paraffins.

Ethylene is recovered from the pressurized fractionation system 730 in a product line 735. Similarly, gasoline is recovered in a product line 746. Ethane and propane are removed in lines 762 and 760, respectively, for recycle to the steam cracking unit 710.

Propylene is removed from the pressurized fractionation system 730 in a line 742 and fed to a disproportionation unit 738 wherein it is self-disproportionated to additional ethylene and butylenes.

The effluent from the disproportionation unit 738 in a line 744 is then recycled to the pressurized fractionation system 730 for separation.

The $C_4$ hydrocarbons are removed from the pressurized fractionation system 730 in a line 748 and fed to a $C_4$ hydrocarbon processing zone 750. In $C_4$ hydrocarbon processing zone 750 the butadienes are hydrogenated to butenes and 1-butene is hydroisomerized to 2-butenes (not shown). The isobutylene in the mixed $C_4$ hydrocarbon stream is then reacted with methanol from a line 782 to produce methyl tertiary butyl ether product in a line 756. The normal butenes are separated from the butanes via extractive distillation (not shown). The 2-butenes are then directed to a skeletal isomerization reactor (not shown) and partially converted to isobutylene. The effluent from the skeletal isomerization reactor is then recycled to the methyl tertiary butyl ether reactor for reaction of the additional isobutylene with methanol (not shown). The butanes removed in the extractive distillation unit are recycled in a line 758 to steam cracking unit 710. Hydrogen is supplied to the $C_4$ hydrocarbon processing unit via a line 776.

The recycle propane, ethane and butanes in lines 760, 762 and 758, respectively, are directed to the steam cracking unit 710 for cracking to mainly ethylene and propylene. The effluent from the steam cracking unit 710 in a line 712 is combined with the effluent from the deep catalytic cracking unit 706 in a line 707 for further processing as described above.

EXAMPLE 9

Figure 8:
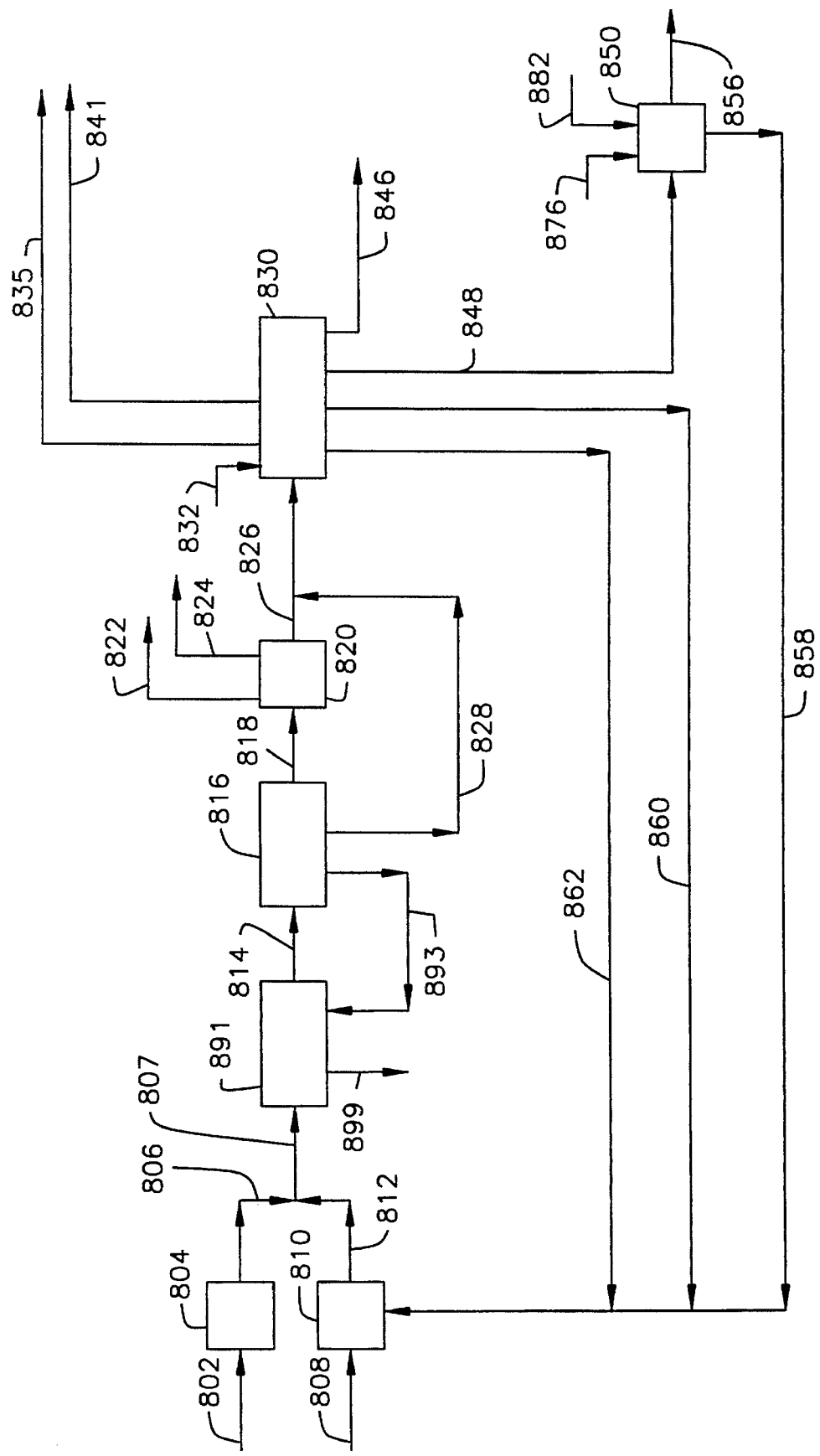
FIG. 8 depicts in flow chart form an embodiment of the present invention with additional ethane feed to the steam cracker.

Referring to FIG. 8, which describes deep catalytic cracking integrated with steam cracking which is also fed with an external ethane stream, 25000 BPSD of a vacuum gas oil in a line 802 are fed to a deep catalytic cracking unit 804. The cracked effluent from the deep catalytic cracking unit comprising mostly cracked gas, ethylene, propylene, butylenes, light paraffins, gasoline, and diesel and fuel oils is removed via a line 806. Simultaneously, 5000 BPSD of ethane in a line 808 is fed to a steam cracking unit 810. The cracked effluent from the steam cracking unit comprising mostly cracked gas, ethylene, propylene and heavier components is removed via a line 812.

The two reactor effluents, in lines 806 and 812, respectively, are combined in a line 807 and directed to an atmospheric fractionator 891 where diesel and fuel oils are removed via a line 899.

The effluent in a line 814 from the atmospheric fractionator 891 comprising mostly cracked gas, ethylene, propylene, butylenes, light paraffins, gasoline and remaining diesel and fuel oils is directed to a compression system 816. The compression system 816 preferably comprises a series of compressors and knock out drums and fractionation tower(s) (not shown) as is known to those skilled in the art. In the compression system 816, remaining diesel and fuel oils are removed and recycled to the atmospheric tower 891 via a recycle line 893. Additionally, gasoline removed in the compression system 816 is directed to the pressurized fractionation system 830 via a by-pass line 828.

The effluent from the compression system in a line 818 comprising mainly cracked gas, ethylene, propylene, butylenes and light paraffins is fed to a chilling train 820 wherein hydrogen and methane are removed in lines 822 and 824, respectively. The remaining effluent in a line 826 comprising mainly ethylene, propylene, butylenes and light paraffins is combined with the by-pass line 828 and fed to a pressurized fractionation unit 830 for separation into its component parts. Additionally, hydrogen is added via a line 832 for hydrogenation of $C_2$ and $C_3$ acetylenes to olefins and paraffins.

Ethylene and propylene are removed from the pressurized fractionation system 830 in product lines 835 and 841, respectively. Similarly, gasoline is recovered in a product line 846. Ethane and propane are removed in lines 862 and 860, respectively, for recycle to the steam cracking unit 810. The $C_4$ hydrocarbons are removed in a line 848 and fed to a $C_4$ hydrocarbon processing zone 850.

In $C_4$ hydrocarbon processing zone 850 the butadienes are first selectively hydrogenated to butenes (not shown). The isobutylene in the $C_4$ hydrocarbons is reacted with methanol from a line 882 to produce methyl tertiary butyl ether product in a line 856. The remaining $C_4$ olefins are further hydrogenated to butanes and recycled in a line 858 to steam cracking unit 810. Hydrogen is supplied to the $C_4$ hydrocarbon processing unit via a line 876.

EXAMPLE 10

Figure 9:
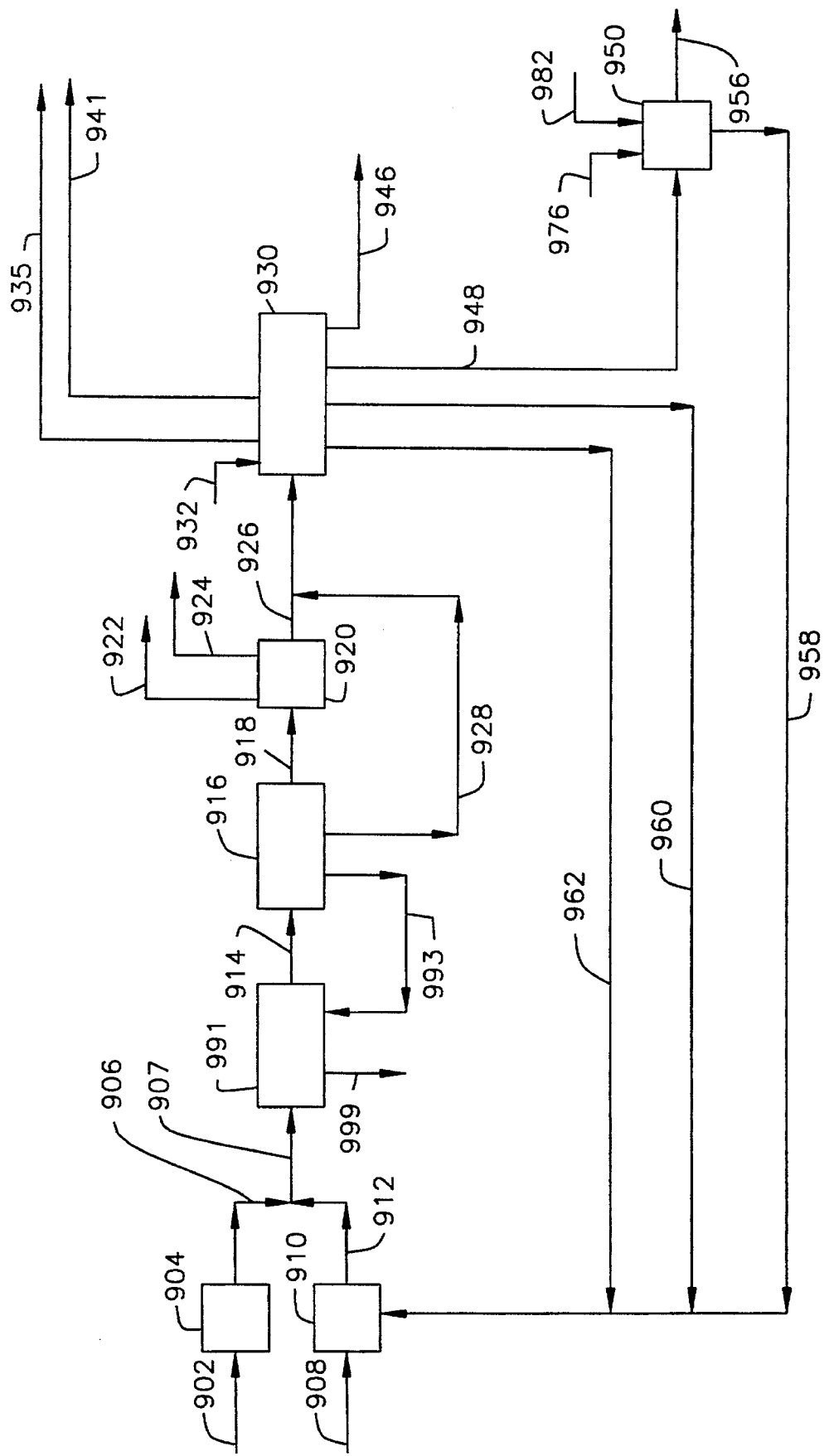
FIG. 9 depicts in flow chart form an embodiment of the present invention with additional propane feed to the steam cracker.

Referring to FIG. 9, which describes deep catalytic cracking integrated with steam cracking which is also fed with an external propane stream, 25000 BPSD of a vacuum gas oil in a line 902 are fed to a deep catalytic cracking unit 904. The cracked effluent from the deep catalytic cracking unit comprising mostly cracked gas, ethylene, propylene, butylenes, light paraffins, gasoline, and diesel and fuel oils is removed via a line 906. Simultaneously, 5000 BPSD of propane in a line 908 is fed to a steam cracking unit 910. The cracked effluent from the steam cracking unit comprising mostly cracked gas, ethylene, propylene and heavier components is removed via a line 912.

The two reactor effluents, in lines 906 and 912, respectively, are combined in a line 907 and directed to an atmospheric fractionator 991 where diesel and fuel oils are removed via a line 999.

The effluent in a line 914 from the atmospheric fractionator 991 comprising mostly cracked gas, ethylene, propylene, butylenes, light paraffins, gasoline and remaining diesel and fuel oils is directed to a compression system 916. The compression system 916 preferably comprises a series of compressors and knock out drums and fractionation tower(s) (not shown) as is known to those skilled in the art. In the compression system 916, remaining diesel and fuel oils are removed and recycled to the atmospheric tower 991 via a recycle line 993. Additionally, gasoline removed in the compression system 916 is directed to the pressurized fractionation system 930 via a by-pass line 928.

The effluent from the compression system in a line 918 comprising mainly cracked gas, ethylene, propylene, butylenes and light paraffins is fed to a chilling train 920 wherein hydrogen and methane are removed in lines 922 and 924, respectively. The remaining effluent in a line 926 comprising mainly ethylene, propylene, butylenes and light paraffins is combined with by-pass line 928 and fed to pressurized fractionation unit 930 for separation into its component parts. Additionally, hydrogen is added via a line 932 for hydrogenation of $C_2$ and $C_3$ acetylenes to olefins and paraffins.

Ethylene and propylene are removed from pressurized fractionation system 930 in product lines 935 and 941, respectively. Similarly, gasoline is recovered in a product line 946. Ethane and propane are removed in lines 962 and 960, respectively, for recycle to the steam cracking unit 910. The $C_4$ hydrocarbons are removed in a line 948 and fed to a $C_4$ hydrocarbon processing zone 950.

In $C_4$ hydrocarbon processing zone 950 the butadienes are first selectively hydrogenated to butenes (not shown). The isobutylene in the $C_4$ hydrocarbons is reacted with methanol from a line 982 to produce methyl tertiary butyl ether product in a line 956. The remaining $C_4$ olefins are further hydrogenated to butanes and recycled in a line 958 to the steam cracking unit 910. Hydrogen is supplied to the $C_4$ hydrocarbon processing unit via a line 976.

TABLE 4

| | Example | | | | | | |
|---|---|---|---|---|---|---|---|
| | 4 | 5 | 6 | 7 | 8 | 9 | 10 |
| Feedstock | | | | | | | |
| Gas oil, bpsd | 25000 | 25000 | 25000 | 25000 | 25000 | 25000 | 25000 |
| Propane, bpsd | — | — | — | — | — | 5000 | — |
| Ethane, bpsd | — | — | — | — | — | — | 5000 |

TABLE 4-continued

| | Example | | | | | | |
|---|---|---|---|---|---|---|---|
| | 4 | 5 | 6 | 7 | 8 | 9 | 10 |
| Products | pounds per hour | | | | | | |
| Hydrogen | 2941 | 2820 | 3536 | 3558 | 3508 | 4721 | 3448 |
| Fuel Gas | 11600 | 23477 | 15476 | 14998 | 15996 | 25292 | 33542 |
| Ethylene | 18061 | 45627 | 28166 | 8226 | 47052 | 65552 | 62117 |
| Propylene | 54201 | 62814 | 56945 | 110323 | — | 63868 | 68731 |
| MTBE | 21242 | 22368 | 73423 | 22230 | 121119 | 22828 | 23141 |
| Gasoline | 57978 | 63837 | 61916 | 61567 | 69225 | 64740 | 67123 |
| Diesel/Fuel Oil | 79657 | 79596 | 79685 | 79641 | 79580 | 79572 | 79548 |
| Coke | 34848 | 35107 | 35056 | 35053 | 35061 | 35239 | 35315 |
| $C_4$ Raffinate | 42000 | — | — | — | — | — | — |
| $C_2/C_3$ | 12708 | — | — | — | — | — | — |
| | metric tons per annum[a] | | | | | | |
| ethylene | 65500 | 165600 | 102200 | 29900 | 170700 | 237900 | 225400 |
| propylene | 196700 | 227900 | 206600 | 40300 | — | 231800 | 249400 |
| MTBE | 77100 | 81200 | 266400 | 80700 | 439500 | 82800 | 84000 |

[a] = Based on 8000 hrs/year

From TABLE 4 above it can be seen that the process of the present invention provides excellent flexibility in producing significant yields of desired olefins and olefin products. For example, the process can readily be designed to provide improved yields of ethylene and propylene (Examples 5, 9 and 10), propylene and MTBE (Example 6), propylene (Example 7) and ethylene and MTBE (Example 8).

All of the above-referenced patents, patent applications and publications are hereby incorporated by reference in their entirety.

Many variations of the present invention will suggest themselves to those skilled in the art in light of the above-detailed description. For example, a wide variety of hydrocarbon feedstocks can be employed as feeds to the deep catalytic cracking process or the steam cracking process. Further, a variety of other $C_4$ processing alternatives may be carried out in accordance with the present invention. Still further, processes employing a number of alternative recycle streams, such as recycling portions of the product effluent from the deep catalytic cracking unit directly to the steam cracking unit, are contemplated by the present invention. It is also contemplated by the present invention to add an external $C_2$-$C_4$ feedstock to supplement the $C_2$-$C_4$ produced in the process of the present invention, if necessary. It is further contemplated that a mixed $C_5$ hydrocarbon-rich stream may be produced in the olefins purification zone, or other processing zone, which can in turn be further processed, such as in a tertiary amyl methyl ether unit. All such obvious modifications are within the full intended scope of the appended claims.

I claim:

1. An integrated process for the selective production of olefins from hydrocarbons comprising:
   (a) cracking a first hydrocarbon feedstock in a deep catalytic cracking process comprising contacting said heavy hydrocarbon feedstock with a solid, acidic catalyst selected from the group consisting of pentasil shape selective molecular sieves, ultrastable hydrogen Y sieves and a mixture of ultrastable hydrogen Y sieves and pentasil shape selective molecular sieves, in a fluidized or moving bed or dense phase transfer line reactor, in the presence of steam at a temperature in the range of from about 500° C. to about 650° C. and a pressure in the range of from about $1.5\times10^5$ to about $3.0\times10^5$ Pa with a weight hourly space velocity of from about 0.2 to about 20 $hr^{-1}$, a catalyst-to-feedstock ratio of from about 2 to about 12, and a steam-to-feedstock ratio of from about 0.01 to about 2:1 by weight to produce a first olefin-containing effluent;
   (b) cracking a second hydrocarbon feedstock in a non-catalytic steam cracking process comprising thermally cracking said second hydrocarbon feedstock in the presence of steam in a radiant zone of a thermal cracking furnace wherein the mixture of said second hydrocarbon feedstock and steam is heated to an outlet temperature of from about 1500° F. to about 1650° F. and cracked in said radiant zone to produce a second olefin-containing effluent;
   (c) combining said first olefin-containing effluent with said second olefin-containing effluent to produce a mixed olefin-containing effluent for downstream processing;
   (d) recycling a portion of said mixed olefin-containing effluent to the steam cracking step (b) as at least a portion of said second hydrocarbon feedstock; and
   (e) recovering an effluent of selectively produced olefins from the mixed olefin-containing effluent from the downstream processing step.

2. A process as defined in claim 1, wherein the selectively produced olefins comprise one or more of ethylene, propylene and butylenes.

3. A process as defined in claim 1, wherein said first hydrocarbon feedstock is selected from the group consisting of crude oil, naphtha, distillate, vacuum gas oil, residual oil and mixtures thereof.

4. A process as defined in claim 1, wherein said first olefin-containing effluent comprises propylene in an amount over about 15 wt. % and butylene in an amount of about 15 wt. %, based on the weight of the feedstock.

5. A process as defined in claim 1 wherein said second hydrocarbon feedstock comprises a light hydrocarbon feedstock selected from the group consisting of gas oils, naphthas, butanes, propane, ethane and mixtures thereof.

6. A process as defined in claim 1, wherein said steam cracking process comprises:
   (i) preheating the second hydrocarbon feedstock in a convection zone of a thermal cracking furnace to a temperature of from about 1100° F. to about 1300° F.;

(ii) mixing steam with said second hydrocarbon feedstock in said convection zone;

(iii) thermally cracking said preheated second hydrocarbon feedstock/steam mixture in a radiant zone of said thermal cracking furnace, whereby said mixture is heated to an outlet temperature of from about 1500° F. to about 1650° F. and cracked in said radiant zone to produce said second olefin-containing effluent; and (iv) cooling said second olefin-containing effluent to a temperature at which the cracking reactions substantially stop.

7. A process as defined in claim 6, wherein said steam cracking process comprises passing said second hydrocarbon/steam mixture through said radiant zone at a velocity of from about 300 to about 800 ft per second, a steam to feed weight ratio ranging from about 0.1 to about 2.0, and a residence time of said second hydrocarbon feedstock in the radiant zone ranging from about 0.1 to about 1.0 second.

8. A process as defined in claim 6, wherein said cooling step (iv) has a residence time ranging from about 1 to about 30 milliseconds.

9. A process as defined in claim 1, wherein said downstream processing step comprises separating said mixed olefin-containing effluent into a plurality of component effluent streams comprising one or more of an ethane-rich stream, a propane-rich stream, an ethylene-rich stream, a propylene-rich stream, a mixed $C_4$ hydrocarbon-rich stream, a gasoline-rich stream, a diesel-rich stream and a fuel oil-rich stream in an olefins purification process.

10. A process as defined in claim 9, wherein said olefins purification process comprises the steps of:

(I) compressing said mixed olefin-containing effluent to a pressure of from about 350 psig to about 520 psig to produce a compressed olefin-containing stream;

(II) chilling the compressed olefin-containing stream to a temperature of from about −185° F. to about −235° F. to produce a chilled compressed olefin-containing stream; and (III) separating the chilled compressed olefin-containing stream in at least one pressurized fractionator into a plurality of component effluent streams comprising one or more of an ethane-rich stream, a propane-rich stream, an ethylene-rich stream, a propylene-rich stream, a mixed $C_4$ hydrocarbon-rich stream and a gasoline-rich stream.

11. A process as defined in claim 9 wherein said portion of said mixed olefin-containing effluent which is recycled to said steam cracking step comprises said ethane-rich stream.

12. A process as defined in claim 9 wherein said portion of said mixed olefin-containing effluent which is recycled to said steam cracking step comprises said propane-rich stream.

13. A process as defined in claim 9, wherein the olefins purification process comprises a compression system and a cryogenic separation process for recovering a plurality of component effluent streams comprising one or more of an ethane-rich stream, a propane-rich stream, an ethylene-rich stream, a propylene-rich stream, a mixed $C_4$ hydrocarbon-rich stream, and a gasoline-rich stream from said mixed olefin-containing effluent, wherein said cryogenic separation process comprises:

(A) introducing said mixed olefin containing-effluent into a dephlegmation or separation zone operating at cryogenic temperatures;

(B) dephlegmating or separating said mixed olefin-containing effluent into a primary methane-rich gas stream and a primary liquid condensate stream rich in $C_2^+$ hydrocarbon components and containing a minor amount of methane;

(C) separating said primary liquid condensate stream in a moderately low cryogenic temperature primary demethanizer unit into a $C_2^+$ liquid bottoms stream and an intermediate methane-rich overhead vapor stream;

(D) separating said intermediate methane-rich overhead vapor stream in an ultra low cryogenic temperature final demethanizer into an ethylene-rich hydrocarbon product stream and a final demethanizer ultra-low temperature vapor stream;

(E) separating said $C_2^+$ liquid bottoms stream in at least one downstream fractionator into effluent streams comprising one or more of an ethane-rich stream, a propane-rich stream, a propylene-rich stream, a $C_4$ hydrocarbon-rich stream, and a gasoline-rich stream.

14. A process as defined in claim 13 further comprising separating and withdrawing at least a portion of the diesel oil and fuel oil from said mixed olefin-containing effluent stream in an atmospheric fractionator upstream of said compression system and cryogenic separation process.

15. A process as defined in claim 10 further comprising a disproportionation process downstream of the olefins purification process, said disproportionation process comprising either:

(1) disproportionating at least a portion of the ethylene in said ethylene-rich stream with at least a portion of the normal butenes from said mixed $C_4$ hydrocarbon-rich stream in the presence of a disproportionation catalyst at a temperature ranging from about 0° to about 600° C., a pressure ranging from about 0.1 to about 500 atmospheres, and with a contact time ranging from about 0.1 second to about 24 hours to produce a disproportionation effluent rich in propylene; or (2) disproportionating at least a portion of the propylene in said propylene-rich stream in the presence of a disproportionation catalyst at a temperature ranging from about 0° to about 600° C., a pressure ranging from about 0.1 to about 500 atmospheres, and with a contact time ranging from about 0.1 second to about 24 hours to produce a disproportionation effluent rich in ethylene and normal butylenes.

16. A process as defined in claim 15 wherein said disproportionation catalyst comprises an inorganic oxide containing a catalytic amount of a metal or metal oxide.

17. A process as defined in claim 13 further comprising recycling said disproportionation effluent to said olefin purification process.

18. A process as defined in claim 15 wherein said disproportionation process is carried out in the liquid phase in the presence of a diluent selected from the group consisting of liquid aliphatic saturated hydrocarbons, cyclohexane, aromatic hydrocarbons and mixtures thereof.

19. A process as defined in claim 15 wherein said disproportionation process is carried out in the gaseous phase in the presence of a diluent selected from the group consisting of gaseous aliphatic saturated hydrocarbons, inert gases and mixtures thereof.

20. A process as defined in claim 15 wherein said disproportionation process is effected continuously in a disproportionation reactor having a catalyst bed selected from the group consisting of a fixed catalyst bed, a slurried catalyst bed, and a fluidized catalyst bed.

21. A process as defined in claim 9 further comprising processing said $C_4$ hydrocarbon-rich stream in a $C_4$ hydrocarbon processing zone.

22. A process as defined in claim 21 wherein said $C_4$ hydrocarbon processing zone comprises a methyl tertiary butyl ether synthesis step comprising reacting at least a portion of the isobutylene in said $C_4$ hydrocarbon-rich stream with methanol in the presence of an acidic ion exchange resin catalyst to produce a synthesis product effluent stream rich in methyl tertiary butyl ether and a by-product effluent stream rich in $C_4$ hydrocarbons.

23. A process as defined in claim 22 wherein said catalyst is selected from the group consisting of sulfonated coals, phenol formaldehyde resins reacted with sulfuric acid, sulfonated resinous polymers of cumarone-indene with cyclopentadiene, divinylbenzene polystyrene copolymers and mixtures thereof.

24. A process as defined in claim 22 wherein said methyl tertiary butyl ether synthesis reaction is carried out at a mole ratio of methanol to isobutylene ranging from about 0.1 to about 5 and a temperature ranging from about 60° F. to about 300° F.

25. A process as defined in claim 22 further comprising recycling said by-product effluent to the steam cracking process as a portion of said second hydrocarbon feedstock.

26. A process as defined in claim 21 wherein said $C_4$ hydrocarbon processing zone comprises:

(I) hydrogenating at least a portion of the butadienes in said $C_4$ hydrocarbon-rich stream to produce a hydrogenated $C_4$ hydrocarbon-rich stream;

(II) reacting at least a portion of the isobutylene in said hydrogenated $C_4$ hydrocarbon-rich stream with methanol in a methyl tertiary butyl ether synthesis reactor in the presence of an acid type ion exchange resin catalyst to produce an ether synthesis product effluent stream rich in methyl tertiary butyl ether and a synthesis by-product effluent stream containing $C_4$ paraffins and $C_4$ olefins;

(III) separating at least a portion of the $C_4$ paraffins from the $C_4$ olefins in said synthesis by-product effluent to produce a $C_4$ paraffin-rich effluent and a $C_4$ olefin-rich effluent; and (IV) converting at least a portion of the normal butenes in said $C_4$ olefin-rich effluent to isobutylene in the presence of an acidic skeletal isomerization catalyst at a pressure of about atmospheric pressure and a temperature ranging from about 600° F. to about 1100° F. to produce an isobutylene enriched effluent.

27. A process as defined in claim 26 wherein said butadiene hydrogenation step (I) comprises catalytically hydrogenating substantially all of the acetylenes and dienes in said mixed $C_4$ hydrocarbon-rich stream to butenes, and catalytically hydroisomerizing at least a portion of the 1-butene in said mixed $C_4$ hydrocarbon-rich stream to 2-butenes.

28. A process as defined in claim 27 wherein said hydroisomerization is carried out at a temperature ranging from about 40° C. to about 400° C., a pressure ranging from about 1 to about 100 bar and a space velocity ranging from about 0.5 to about 20 kg hydrocarbon feed/kg catalyst hour in the presence of a hydroisomerization catalyst comprising at least one hydrogenating metal and a moderately acidic carrier.

29. A process as defined in claim 26 wherein said paraffin/olefin separation step (III) comprises separating at least a portion of the $C_4$ paraffins from the $C_4$ olefins by extractive distillation, selective membrane distillation and/or molecular sieve separation.

30. A process as defined in claim 29 wherein said paraffin/olefin separation step (III) comprises extractive distillation.

31. A process as defined in claim 30 wherein said extractive distillation comprises separating at least a portion of the $C_4$ paraffins from the $C_4$ olefins in said synthesis by-product effluent in a tower in the presence of a solvent selected from the group consisting of tetrahydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing; whereby said synthesis by-product effluent is separated into a $C_4$ paraffin-rich effluent substantially comprising $C_3$ and lighter boiling hydrocarbons, isobutane and n-butane, and a $C_4$ olefin-rich effluent substantially comprising cis-2-butene, trans-2-butene and 1-butene.

32. A process as defined in claim 31 wherein all or a portion of said $C_4$ olefin-rich stream is fed to a disproportionation process for disproportionation with ethylene in the presence of a disproportionation catalyst at a temperature ranging from about 0° to about 600° C., a pressure ranging from about 0.1 to about 500 atmospheres, and with a contact time ranging from about 0.1 second to about 24 hours to produce a disproportionation effluent rich in propylene.

33. A process as defined in claim 26 further comprising recycling said isobutylene enriched effluent to said methyl tertiary butyl ether synthesis reactor for conversion into methyl tertiary butyl ether.

34. A process as defined in claim 26 wherein said portion of said mixed olefin-containing effluent which is recylced to said steam cracking step comprises said $C_4$ parrafin-rich effluent.

35. An integrated process for the selective production of olefins from hydrocarbons comprising:

(a) cracking a first hydrocarbon feedstock in a deep catalytic cracking process comprising contacting said first hydrocarbon feedstock with a solid, acidic catalyst selected from the group consisting of pentasil shape selective molecular sieves, ultrastable hydrogen Y sieves and a mixture of ultrastable hydrogen Y sieves and pentasil shape selective molecular sieves, in a fluidized or moving bed or dense phase transfer line reactor, in the presence of steam at a temperature in the range of from about 500° C. to about 650° C. and a pressure in the range of from about $1.5 \times 10^5$ to about $3.0 \times 10^5$ Pa with a weight hourly space velocity of from about 0.2 to about 20 $hr^{-1}$, a catalyst-to-feedstock weight ratio of from about 2 to about 12, and a steam-to-feedstock ratio of from about 0.01 to about 2:1 by weight to produce a first olefin-containing effluent;

(b) cracking a second hydrocarbon feedstock in a non-catalytic steam cracking process comprising thermally cracking said second hydrocarbon feedstock in the presence of steam in a radiant zone of a thermal cracking furnace wherein the mixture of said second hydrocarbon feedstock and steam is heated to an outlet temperature of from about 1500° F. to about 1650° F. and cracked in said radiant zone to produce said second olefin-containing effluent;

(c) combining said first olefin-containing effluent with said second olefin-containing effluent to produce a mixed olefin-containing effluent;

(d) separating the mixed olefin-containing effluent in an olefins purification process comprising at least one fractionator into a plurality of component effluent streams comprising one or more of an ethane-rich stream, a propane-rich stream, an ethylene-rich stream, a propylene-rich stream, a mixed $C_4$ hydrocarbon-rich stream, a gasoline-rich stream, a diesel-rich stream and a fuel oil-rich stream; and (e) recycling at least a portion of one or more of said ethane-rich stream, propane-rich stream and/or mixed $C_4$ mixed hydrocarbon-rich stream to said steam cracking step (b) as at least a portion of said second hydrocarbon feedstock.

36. A process as defined in claim 35 wherein said recycling step (e) comprises recycling at least a portion of said ethane-rich stream, at least a portion of said propane-rich stream, or at least a portion of both said ethane-rich stream and said propane rich stream to said steam cracking step (b) as at least a portion of said second hydrocarbon feedstock.

37. A process as defined in claim 35 further comprising a disproportionation process downstream of said olefins purification process, said disproportionation process comprising either:

(1) disproportionating at least a portion of the ethylene in said ethylene-rich stream with at least a portion of the normal butenes from said mixed $C_4$ hydrocarbon-rich stream in the presence of a disproportionation catalyst at a temperature ranging from about 0° to about 600° C., a pressure ranging from about 0.1 to about 500 atmospheres, and with a contact time ranging from about 0.1 seconds to about 24 hours to produce a disproportionation effluent rich in propylene; or (2) disproportionating at least a portion of the propylene in said propylene-rich stream in the presence of a disproportionation catalyst at a temperature ranging from about 0° to about 600° C., a pressure ranging from about 0.1 to about 500 atmospheres, and with a contact time ranging from about 0.1 seconds to about 24 hours to produce a disproportionation effluent rich in ethylene and normal butylenes.

38. A process as defined in claim 37 further comprising recycling said disproportionation effluent to said olefins purification process.

39. A process as defined in claim 35 further comprising a $C_4$ hydrocarbon processing step which comprises (I) hydrogenating at least a portion of the butadienes in said $C_4$ hydrocarbon-rich stream to produce a hydrogenated $C_4$ hydrocarbon-rich stream;

(II) reacting at least a portion of the isobutylene in said hydrogenated $C_4$ hydrocarbon-rich stream with methanol in a methyl tertiary butyl ether synthesis reactor in the presence of an acidic ion exchange resin catalyst to produce an ether synthesis product effluent stream rich in methyl tertiary butyl ether and a synthesis by-product effluent stream containing $C_4$ paraffins and $C_4$ olefins;

(III) separating at least a portion of the $C_4$ paraffins from the $C_4$ olefins in said synthesis by-product to produce a $C_4$ paraffin-rich effluent and a $C_4$ olefin-rich effluent; and (IV) converting at least a portion of the normal butenes in said $C_4$ olefin-rich effluent to isobutylene in the presence of an acidic skeletal isomerization catalyst at a pressure of about atmospheric pressure and a temperature ranging from about 600° F. to about 1100° F. to produce an isobutylene enriched effluent.

40. A process as defined in claim 39 further comprising recycling said by-product effluent to the steam cracking process (d) as a component of said second hydrocarbon feedstock.

41. A process as defined in claim 39 wherein said butadiene hydrogenation step (I) comprises a hydroisomerization process of catalytically converting substantially all of the acetylenes and dienes in said mixed $C_4$ hydrocarbon-rich stream to butenes, and catalytically converting at least a portion of the 1-butene in said mixed $C_4$ hydrocarbon-rich stream to 2-butenes; wherein said hydroisomerization is carried out at a temperature ranging from about 40° C. to about 400° C., a pressure ranging from about 1 to about 100 bar and a space velocity ranging from about 0.5 to 20 kg hydrocarbon feed/kg catalyst hour in the presence of a hydroisomerization catalyst comprising at least one hydrogenating metal and a moderately acidic carrier.

42. A process as defined in claim 39 wherein said paraffin/olefin separation step (III) is an extractive distillation process comprising separating at least a portion of the $C_4$ paraffins from the $C_4$ olefins in said synthesis by-product effluent in a tower in the presence of a solvent selected from the group consisting of tetrahydrofuran, diethyl ketone, diethyl carbonate, methyl ethyl ketone, pentanedione, cyclopentanone, acetone, butyronitrile, acetyl piperidine, acetophenone, pyridine, diethyl oxalate, propionitrile, dimethyl acetamide, n-methyl pyrrolidone, acetonyl acetone, tetrahydrofurfuryl alcohol, dimethyl sulfolane, dimethyl cyanamide, methyl carbitol, dimethyl formamide, methyl cellosolve, furfural, acetonitrile, ethylene chlorhydrin, gamma-butyrolactone, methanol, beta-chloropropionitrile, pyrrolidone, propylene carbonate, nitromethane, ethylene diamine and mixtures of any of the foregoing; whereby said synthesis by-product effluent is separated into a $C_4$ paraffin-rich effluent substantially comprising $C_3$ and lighter boiling hydrocarbons, isobutane and n-butane, and a $C_4$ olefin-rich effluent substantially comprising cis-2-butene, trans-2-butene and 1-butene.

43. An integrated process for the improved production of propylene from hydrocarbons which comprises:

(a) cracking a first hydrocarbon feedstock in a deep catalytic cracking process comprising contacting said first hydrocarbon feedstock with a solid, acidic catalyst selected from the group consisting of pentasil shape selective molecular sieves, ultrastable hydrogen Y sieves and a mixture of ultrastable hydrogen Y sieves and pentasil shape selective molecular sieves in a fluidized or moving bed or dense phase transfer line reactor, in the presence of steam at a temperature in the range of from about 500° C. to about 650° C. and a pressure in the range of from about $1.5 \times 10^5$ to about $3.0 \times 10^5$ Pa with a weight hourly space velocity of from about 0.2 to about 20 $hr^{-1}$, a catalyst-to-feedstock ratio of from about 2 to about 12, and a steam-to-feedstock ratio of from about 0.01 to about 2:1 by weight to produce a first olefin-containing effluent;

(b) cracking a second hydrocarbon feedstock in a non-catalytic steam cracking process comprising thermally cracking said second hydrocarbon feedstock in the presence of steam in a radiant zone of a thermal cracking furnace wherein the mixture of said second hydrocarbon feedstock and steam is heated to an outlet temperature of from about 1500° F. to about 1650° F. and cracked in said radiant zone to produce a second olefin-containing effluent;

(c) combining said first olefin-containing effluent and said second olefin-containing effluent to produce a mixed olefin-containing effluent;

(d) separating said mixed olefin-containing effluent in an olefins purification process comprising at least one fractionator into a plurality of component effluent streams comprising one or more of an ethane-rich stream, a propane-rich stream, an ethylene-rich stream, a propylene-rich stream, a mixed $C_4$ hydrocarbon-rich stream, a gasoline-rich stream, a diesel-rich stream and a fuel oil-rich stream;

(e) recycling one or more of at least a portion of said ethane-rich stream, said propane-rich stream, said mixed $C_4$ hydrocarbon rich stream or said gasoline-rich stream to said steam cracking process (b) as at least a portion of said second hydrocarbon feedstock;

(f) disproportionating at least a portion of the ethylene in said ethylene-rich stream with at least a portion of the normal butenes from said mixed $C_4$ hydrocarbon-rich stream in the presence of a disproportionation catalyst at a temperature ranging from about 0° to about 600° C., a pressure ranging from about 0.1 to about 500 atmospheres, and with a contact time ranging from about 0.1 seconds to about 24 hours to produce a disproportionation effluent rich in propylene;

(g) recycling said disproportionation effluent to said olefins purification process; and (h) recovering said propylene-rich stream from said olefins purification process.

44. A process as defined in claim 43 further comprising a $C_4$ hydrocarbon processing zone comprising:

(I) hydroisomerizing said mixed $C_4$ hydrocarbon-rich stream to catalytically convert substantially all of acetylenes and dienes in said mixed $C_4$ hydrocarbon-rich stream to butenes, and catalytically converting at least a portion of the 1-butene in said mixed $C_4$ hydrocarbon-rich stream to 2-butenes to produce a hydroisomerized $C_4$ hydrocarbon effluent; and (II) separating at least a portion of the $C_4$ paraffins from the $C_4$ olefins in said hydroisomerized $C_4$ hydrocarbon effluent to produce a $C_4$ paraffin-rich effluent and a $C_4$ olefin-rich effluent; and (III) directing said $C_4$ olefin-rich effluent to said disproportionation reactor for reaction with ethylene to produce propylene.

45. An integrated process for the improved production of ethylene from hydrocarbons which comprises:

(a) cracking a first hydrocarbon feedstock in a deep catalytic cracking process comprising contacting said first hydrocarbon feedstock with a solid, acidic catalyst selected from the group consisting of pentasil shape selective molecular sieves, ultrastable hydrogen Y sieves and a mixture of ultrastable hydrogen Y sieves and pentasil shape selective molecular sieves, in a fluidized or moving bed or dense phase transfer line reactor, in the presence of steam at a temperature in the range of from about 500° C. to about 650° C. and a pressure in the range of from about $1.5 \times 10^5$ to about $3.0 \times 10^5$ Pa with a weight hourly space velocity of from about 0.2 to about 20 $hr^{-1}$, a catalyst-to-feedstock ratio of from about 2 to about 12, and a steam-to-feedstock ratio of from about 0.01 to about 2:1 by weight to produce a first olefin-containing effluent;

(b) cracking a second hydrocarbon feedstock in a non-catalytic steam cracking process comprising thermally cracking said second hydrocarbon feedstock in the presence of steam in a radiant zone of a thermal cracking furnace wherein the mixture of said second hydrocarbon feedstock and steam is heated to an outlet temperature of from about 1500° F. to about 1650° F. and cracked in said radiant zone to produce a second olefin-containing effluent;

(c) combining said first olefin-containing effluent and second olefin-containing effluent to produce a mixed olefin-containing effluent;

(d) separating said mixed olefin-containing effluent in an olefins purification process comprising at least one fractionator into a plurality of component effluent streams comprising an ethane-rich stream, a propane-rich stream, an ethylene-rich stream, a propylene-rich stream, a $C_4$ hydrocarbon-rich stream, a gasoline-rich stream, a diesel-rich stream and a fuel oil-rich stream;

(e) recycling at least a portion of one or more of said ethane-rich stream, propane-rich stream, mixed $C_4$ hydrocarbon-rich stream or said gasoline-rich stream to said steam cracking process (b) as at least a portion of said second hydrocarbon feedstock;

(f) disproportionating at least a portion of the propylene in said propylene-rich stream in the presence of a disproportionation catalyst at a temperature ranging from about 0° to about 600° C., a pressure ranging from about 0.1 to about 500 atmospheres, and with a contact time ranging from about 0.1 seconds to about 24 hours to produce a disproportionation effluent rich in ethylene and butylenes;

(g) recycling said disproportionation effluent to olefins purification process; and (h) recovering said ethylene-rich stream from said olefins purification process.

46. An integrated process for the selective production of methyl tertiary butyl ether from hydrocarbons comprising:

(a) cracking a first hydrocarbon feedstock in a deep catalytic cracking process comprising contacting said heavy hydrocarbon feedstock with a solid, acidic catalyst selected from the group consisting of pentasil shape selective molecular sieves, ultrastable hydrogen Y sieves and a mixture of ultrastable hydrogen Y sieves and pentasil shape selective molecular sieves, in a fluidized or moving bed or dense phase transfer line reactor, in the presence of steam at a temperature in the range of from about 500° C. to about 650° C. and a pressure in the range of from about $1.5 \times 10^3$ to about $3.0 \times 10^5$ Pa with a weight hourly space velocity of from about 0.2 to about 20 $hr^{-1}$, a catalyst-to-feedstock ratio of from about 2 to about 12, and a steam-to-feedstock ratio of from about 0.01 to about 2:1 by weight to produce a first olefin-containing effluent;

(b) cracking a second hydrocarbon feedstock in a non-catalytic steam cracking process comprising thermally cracking said second hydrocarbon feedstock in the presence of steam in a radiant zone of a thermal cracking furnace wherein the mixture of said second hydrocarbon feedstock and steam is heated to an outlet temperature of from about 1500° F. to about 1650° F. and cracked in said radiant zone to produce a second olefin-containing effluent;

(c) combining said first olefin-containing effluent and said second-olefin containing effluent to produce a mixed olefin-containing effluent;

(d) introducing said mixed olefin-containing effluent into an olefin purification process comprising:

(i) compressing said mixed olefin-containing effluent to a pressure ranging from about 350 to about 520 psig to produce a compressed olefin-containing stream;

(ii) chilling the compressed olefin-containing stream to a temperature ranging from about −185° F. to about −235° F. to produce a chilled compressed olefin-containing stream; and (iii) separating the chilled compressed olefin-containing stream in at least one fractionator into a plurality of component effluent streams comprising at least one of an ethane-rich stream, a propane-rich stream, an ethylene-rich stream, a propylene-rich stream, a mixed $C_4$ hydrocarbon-rich stream and a gasoline-rich stream;

(e) recycling at least a portion of one or more of said ethane-rich stream, said propane-rich stream or said gasoline-rich stream to said steam cracking process (b) as at least a portion of said second hydrocarbon feedstock;

(f) disproportionating at least a portion of the propylene in said propylene-rich stream in the presence of a disproportionation catalyst at a temperature ranging from about 0° C. to about 600° C., a pressure ranging from about 0.1 to about 500 atmospheres, and with a contact time ranging from about 0.1 seconds to about 24 hours to produce a disproportionation effluent rich in ethylene and normal butylenes;

(g) recycling said disproportionation effluent to said olefin purification process;

(h) passing said mixed $C_4$ hydrocarbon-rich stream to a $C_4$ hydrocarbon processing zone comprising:

(1) hydroisomerizing said mixed $C_4$ hydrocarbon-rich stream to catalytically convert substantially all of acetylenes and dienes in said $C_4$ hydrocarbon-rich stream to butenes and catalytically converting at least a portion of the 1-butene in said $C_4$ hydrocarbon-rich stream to 2-butenes; wherein said hydroisomerization is carried out at a temperature ranging from about 40° C. to about 400° C., a pressure ranging from about 1 to about 100 bar and a space velocity ranging from about 0.5 to about 2.0 kg hydrocarbon feed/kg catalyst hour in the presence of a hydroisomerization catalyst comprising at least one hydrogenating metal and a moderately acidic carrier;

(2) reacting at least a portion of the isobutylene in said hydroisomerized $C_4$ hydrocarbon-rich stream with methanol in a methyl tertiary butyl ether synthesis reactor in the presence of an acid type ion exchange resin catalyst to produce an ether synthesis product effluent stream rich in methyl tertiary butyl ether and a synthesis by-product effluent stream;

(3) separating said synthesis by-product effluent stream in an extractive distillation tower in the presence of a solvent into a paraffin-rich stream substantially comprising $C_3$ and lighter boiling hydrocarbons, isobutane and n-butane, and a $C_4$ olefin-rich stream substantially comprising cis-2-butene, trans-2-butene and 1-butene; and (4) converting at least a portion of the normal butenes in said $C_4$ olefin-rich effluent to isobutylene in the presence of an acidic skeletal isomerization catalyst at a pressure of about atmospheric pressure and a temperature ranging from about 600° F. to about 1100° F. to produce an isobutylene enriched effluent;

(i) recycling said isobutylene enriched effluent either to said methyl tertiary butyl ether synthesis reactor, or to the hydroisomerization step; and (j) recovering said ether synthesis product effluent rich in methyl tertiary butyl ether.

47. An integrated process for the selective production of olefins from hydrocarbons comprising:

(a) cracking a first hydrocarbon feedstock in a deep catalytic cracking process comprising contacting said heavy hydrocarbon feedstock with a solid, acidic catalyst selected from the group consisting of pentasil shape selective molecular sieves, ultrastable hydrogen Y sieves and a mixture of ultrastable hydrogen Y sieves and pentasil shape selective molecular sieves, in a fluidized or moving bed or dense phase transfer line reactor, in the presence of steam at a temperature in the range of from about 500° C. to about 650° C. and a pressure in the range of from about $1.5 \times 10^5$ to about $3.0 \times 10^5$ with a weight hourly space velocity of from about 0.2 to about 20 $hr^{-1}$, a catalyst-to-feedstock ratio of from about 2 to about 12, and a steam-to-feedstock ratio of from about 0.01 to about 2:1 by weight to produce a first olefin-containing effluent;

(b) cracking a second hydrocarbon feedstock in a non-catalytic thermal cracking process to produce a second olefin-containing effluent;

(c) combining said first olefin-containing effluent with said second olefin-containing effluent to produce a mixed olefin-containing effluent for downstream processing;

(d) recycling a portion of said mixed olefin-containing effluent to said non-catalytic cracking step (b) as at least a portion of said second hydrocarbon feedstock; and (e) recovering an effluent of selectively produced olefins from the mixed olefin-containing effluent.

* * * * *